US012620462B2

(12) United States Patent
Boussios et al.

(10) Patent No.: US 12,620,462 B2
(45) Date of Patent: *May 5, 2026

(54) INFORMATION SYSTEM PROVIDING EXPLANATION OF MODELS

(71) Applicant: OM1, Inc., Boston, MA (US)

(72) Inventors: Constantinos Ioannis Boussios, Chelsea, MA (US); Richard Gliklich, Weston, MA (US); Francis Thomas O'Donovan, Arlington, MA (US)

(73) Assignee: OM1, Inc., Boston, MA (US)

( * ) Notice: Subject to any disclaimer, the term of this patent is extended or adjusted under 35 U.S.C. 154(b) by 610 days.

This patent is subject to a terminal disclaimer.

(21) Appl. No.: 17/573,725

(22) Filed: Jan. 12, 2022

(65) Prior Publication Data

US 2022/0148695 A1    May 12, 2022

Related U.S. Application Data

(63) Continuation of application No. 15/927,766, filed on Mar. 21, 2018, now Pat. No. 11,257,574.

(Continued)

(51) Int. Cl.
*G16H 10/60*      (2018.01)
*G06N 5/022*      (2023.01)
(Continued)

(52) U.S. Cl.
CPC ............. *G16H 10/60* (2018.01); *G06N 5/022* (2013.01); *G06N 20/00* (2019.01); *G16H 50/70* (2018.01)

(58) Field of Classification Search
None
See application file for complete search history.

(56) References Cited

U.S. PATENT DOCUMENTS

| 5,486,999 A | 1/1996 | Mebane |
| 5,508,912 A | 4/1996 | Schneiderman |

(Continued)

FOREIGN PATENT DOCUMENTS

| EP | 2614480 A2 | 7/2013 |
| WO | 0057310 A1 | 9/2000 |

(Continued)

OTHER PUBLICATIONS

Awan et al., "Machine Learning-Based Prediction of Heart Failure Readmission or Death: Implications of Choosing the Right Model and the Right Metrics", ESC Heart Failure, DOI: 10.1002/ehf2. 12419, vol. 6, Feb. 27, 2019, pp. 428-435.

(Continued)

*Primary Examiner* — Jonathan Ng
(74) *Attorney, Agent, or Firm* — Outside General Counsel LLP; Peter Gordon

(57)    ABSTRACT

A health care information system generates information that describes how different inputs to a model affect the output of the model, by creating a localized model for a given entity, and determining how the output of the localized model for the given entity changes in response to different inputs. The computer system builds the localized model for a given entity based on the model and on data values for the given entity. The computer system inputs one or more different data values for selected input features of the localized model, while data values for the remaining input features of the localized model are fixed to data values for the given entity, and obtains corresponding outputs from the localized model. The results from this localized model for the given entity indicate which of the selected input features have the most impact on the output of the model for that entity.

28 Claims, 26 Drawing Sheets

Related U.S. Application Data

(60) Provisional application No. 62/474,587, filed on Mar. 21, 2017.

(51) Int. Cl.

| | |
|---|---|
| *G06N 20/00* | (2019.01) |
| *G16H 50/70* | (2018.01) |

(56) References Cited

U.S. PATENT DOCUMENTS

| | | | |
|---|---|---|---|
| 5,619,421 A | 4/1997 | Venkataraman et al. | |
| 5,961,332 A | 10/1999 | Joao | |
| 6,101,511 A | 8/2000 | Derose et al. | |
| 6,317,731 B1 | 11/2001 | Luciano | |
| 6,524,241 B2 | 2/2003 | Iliff | |
| 6,687,685 B1 | 2/2004 | Sadeghi et al. | |
| 7,076,437 B1 | 7/2006 | Levy | |
| 7,194,301 B2 | 3/2007 | Jenkins et al. | |
| 7,433,519 B2 | 10/2008 | Rynderman | |
| 7,739,126 B1 | 6/2010 | Cave et al. | |
| 7,809,660 B2 | 10/2010 | Friedlander et al. | |
| 7,916,363 B2 | 3/2011 | Rynderman | |
| 7,930,262 B2 | 4/2011 | Friedlander et al. | |
| 7,949,620 B2 | 5/2011 | Otte et al. | |
| 8,090,590 B2 | 1/2012 | Fotsch et al. | |
| 8,140,541 B2 | 3/2012 | Koss | |
| 8,154,776 B2 | 4/2012 | Rynderman | |
| 8,165,973 B2 | 4/2012 | Alexe et al. | |
| 8,190,451 B2 | 5/2012 | Lloyd et al. | |
| 8,311,849 B2 | 11/2012 | Soto et al. | |
| 8,335,698 B2 | 12/2012 | Angell et al. | |
| 8,392,215 B2 | 3/2013 | Tawil | |
| 8,538,773 B2 | 9/2013 | Morris et al. | |
| 8,560,281 B2 | 10/2013 | Spertus et al. | |
| 8,583,586 B2 | 11/2013 | Ebadollahi et al. | |
| 8,930,223 B2 | 1/2015 | Friedlander et al. | |
| 9,514,416 B2 | 12/2016 | Lee et al. | |
| 9,646,271 B2 | 5/2017 | Friedlander et al. | |
| 9,690,844 B2 | 6/2017 | Mukherjee et al. | |
| 10,061,812 B2 | 8/2018 | Marshall et al. | |
| 10,282,512 B2 | 5/2019 | Bennett et al. | |
| 10,311,363 B1 | 6/2019 | Florissi et al. | |
| 10,311,975 B2 | 6/2019 | Young et al. | |
| 10,706,329 B2 | 7/2020 | Anushiravani et al. | |
| 10,731,223 B2 | 8/2020 | Kennedy et al. | |
| 10,731,233 B2 | 8/2020 | Yamada et al. | |
| 11,257,574 B1 | 2/2022 | Boussios et al. | |
| 11,527,326 B2 | 12/2022 | McNair et al. | |
| 11,594,310 B1 | 2/2023 | Bradley et al. | |
| 11,594,311 B1 | 2/2023 | Bradley et al. | |
| 11,862,346 B1 | 1/2024 | Boussios et al. | |
| 11,967,428 B1 | 4/2024 | Boussios et al. | |
| 12,057,204 B2 | 8/2024 | Bradley et al. | |
| 12,142,355 B2 | 11/2024 | Bradley et al. | |
| 2003/0014284 A1 | 1/2003 | Jones | |
| 2004/0122706 A1 | 6/2004 | Walker et al. | |
| 2004/0122707 A1 | 6/2004 | Sabol et al. | |
| 2004/0243362 A1 | 12/2004 | Liebman | |
| 2006/0058384 A1 | 3/2006 | Hogg | |
| 2006/0129427 A1* | 6/2006 | Wennberg | G06Q 10/00 703/2 |
| 2006/0129428 A1 | 6/2006 | Wennberg | |
| 2006/0173663 A1 | 8/2006 | Langheier et al. | |
| 2007/0021979 A1 | 1/2007 | Cosentino et al. | |
| 2007/0172907 A1 | 7/2007 | Volker et al. | |
| 2007/0255113 A1 | 11/2007 | Grimes | |
| 2008/0171916 A1 | 7/2008 | Feder et al. | |
| 2008/0208813 A1 | 8/2008 | Friedlander et al. | |
| 2008/0235049 A1* | 9/2008 | Morita | G16H 50/20 705/2 |
| 2008/0294459 A1 | 11/2008 | Angell et al. | |
| 2009/0119337 A1 | 5/2009 | Biedermann | |
| 2009/0164237 A1 | 6/2009 | Hunt et al. | |
| 2009/0259494 A1 | 10/2009 | Feder et al. | |
| 2009/0287503 A1 | 11/2009 | Angell et al. | |
| 2010/0021956 A1* | 1/2010 | Shearer | G01N 33/92 435/29 |
| 2010/0191088 A1 | 7/2010 | Anderson et al. | |
| 2010/0240035 A1 | 9/2010 | Jablons et al. | |
| 2010/0324927 A1 | 12/2010 | Tinsley | |
| 2011/0010328 A1 | 1/2011 | Patel et al. | |
| 2011/0071363 A1 | 3/2011 | Montijo et al. | |
| 2011/0106558 A1 | 5/2011 | Solito et al. | |
| 2011/0125680 A1* | 5/2011 | Bosworth | G16H 50/20 706/54 |
| 2011/0177956 A1 | 7/2011 | Korenberg | |
| 2011/0288877 A1 | 11/2011 | Ofek et al. | |
| 2012/0065987 A1 | 3/2012 | Farooq et al. | |
| 2012/0084064 A1 | 4/2012 | Dzenis et al. | |
| 2012/0110016 A1 | 5/2012 | Phillips | |
| 2012/0179478 A1 | 7/2012 | Ross | |
| 2012/0191640 A1 | 7/2012 | Ebadollahi et al. | |
| 2012/0215560 A1 | 8/2012 | Ofek et al. | |
| 2012/0254098 A1 | 10/2012 | Flinn et al. | |
| 2012/0296675 A1 | 11/2012 | Silverman | |
| 2013/0185231 A1 | 7/2013 | Baras et al. | |
| 2014/0006447 A1 | 1/2014 | Friedlander et al. | |
| 2014/0074510 A1* | 3/2014 | McClung | G16H 50/30 705/3 |
| 2014/0081898 A1 | 3/2014 | Saigal et al. | |
| 2014/0095204 A1 | 4/2014 | Fung et al. | |
| 2014/0108044 A1 | 4/2014 | Reddy et al. | |
| 2014/0164022 A1 | 6/2014 | Reed et al. | |
| 2014/0249834 A1 | 9/2014 | D'souza et al. | |
| 2014/0350954 A1 | 11/2014 | Ellis et al. | |
| 2015/0106109 A1 | 4/2015 | Crowley et al. | |
| 2015/0106115 A1 | 4/2015 | Hu et al. | |
| 2015/0235001 A1 | 8/2015 | Fouts | |
| 2015/0339442 A1 | 11/2015 | Oleynik | |
| 2015/0347599 A1 | 12/2015 | Mcmains et al. | |
| 2016/0004840 A1 | 1/2016 | Rust et al. | |
| 2016/0012202 A1 | 1/2016 | Hu et al. | |
| 2016/0015347 A1 | 1/2016 | Bregman-Amitai et al. | |
| 2016/0029919 A1 | 2/2016 | Hebert et al. | |
| 2016/0078183 A1 | 3/2016 | Trygstad et al. | |
| 2016/0120481 A1 | 5/2016 | Li et al. | |
| 2016/0188814 A1 | 6/2016 | Raghavan et al. | |
| 2016/0188834 A1 | 6/2016 | Erdmann et al. | |
| 2016/0196394 A1 | 7/2016 | Chanthasiriphan et al. | |
| 2016/0235373 A1 | 8/2016 | Sharma et al. | |
| 2016/0283679 A1 | 9/2016 | Hu et al. | |
| 2016/0283686 A1 | 9/2016 | Hu et al. | |
| 2016/0354039 A1 | 12/2016 | Soto et al. | |
| 2017/0046602 A1 | 2/2017 | Hu et al. | |
| 2017/0061093 A1* | 3/2017 | Amarasingham | G16H 10/60 |
| 2017/0124263 A1 | 5/2017 | Crafts et al. | |
| 2017/0124279 A1 | 5/2017 | Rothman | |
| 2017/0147777 A1 | 5/2017 | Kin et al. | |
| 2017/0235887 A1 | 8/2017 | Cox et al. | |
| 2017/0262609 A1 | 9/2017 | Perlroth et al. | |
| 2017/0323075 A1* | 11/2017 | Krause | G16H 10/60 |
| 2018/0268937 A1 | 9/2018 | Spetzler et al. | |
| 2018/0330805 A1 | 11/2018 | Cheung et al. | |
| 2018/0336319 A1 | 11/2018 | Itu et al. | |
| 2019/0079938 A1 | 3/2019 | Agrawal et al. | |
| 2019/0244714 A1 | 8/2019 | Morra et al. | |
| 2021/0098090 A1 | 4/2021 | Thomas et al. | |
| 2023/0197223 A1 | 6/2023 | Bradley et al. | |
| 2023/0197224 A1 | 6/2023 | Bradley et al. | |
| 2024/0096500 A1 | 3/2024 | Boussios et al. | |
| 2024/0153647 A1 | 5/2024 | Boussios et al. | |
| 2024/0290491 A1 | 8/2024 | Boussios et al. | |

FOREIGN PATENT DOCUMENTS

| | | |
|---|---|---|
| WO | 0209004 A1 | 1/2002 |
| WO | 0209580 A1 | 2/2002 |
| WO | 2003/104939 A2 | 12/2003 |
| WO | 2006/086181 A1 | 8/2006 |
| WO | 2007/050147 A1 | 5/2007 |
| WO | 2008048662 A2 | 4/2008 |
| WO | 2008079341 A2 | 7/2008 |

(56) References Cited

FOREIGN PATENT DOCUMENTS

| WO | 2012019000 A2 | 2/2012 |
| WO | 2014028541 A1 | 2/2014 |
| WO | 2015169810 A1 | 11/2015 |

OTHER PUBLICATIONS

Dua et al., "Machine Learning in Healthcare Informatics", Intelligent Systems Reference Library, Springer, vol. 56, 2014, 334 Pages.

U.S. Patent and Trademark Office, "Final Office Action Received", U.S. Appl. No. 16/386,123, Mar. 31, 2023, 59 Pages.

U.S. Patent and Trademark Office, "Non-Final Office Action Received", U.S. Appl. No. 18/169,363, Jul. 7, 2023, 48 Pages.

U.S. Patent and Trademark Office, "Notice of Allowance Received", U.S. Appl. No. 16/724,264, Sep. 6, 2023, 7 Pages.

U.S. Patent and Trademark Office, "Notice of Allowance Received", U.S. Appl. No. 15/465,550, Jan. 26, 2023, 8 Pages.

U.S. Patent and Trademark Office, "Notice of Allowance Received", U.S. Appl. No. 16/724,264, May 22, 2023, 8 Pages.

Bertens, et al., "A nomogram was developed to enhance the use of multinomial logistic regression modeling in diagnostic research", Mar. 2016, Journal of Clinical Epidemiology, pp. 51-57. (Year: 2016).

Cheng, et al., "Risk Prediction with Electronic Health Records: A Deep Learning Approach", Proceedings of the SIAM International Conference on Data Mining, Jun. 2016, 9 Pages.

Clockbackward, "Ordinary Least Squares Linear Regression: Flaws, Problems and Pitfalls", Jun. 18, 2009, 16 Pages.

Grossman, et al., "Learning Bayesian Network Classifiers by Maximizing Conditional Likelihood", Department of Computer Science and Engineering, University of Washington, Seattle, WA, 2004 (Year: 2004), 8 Pages.

Hileman, "Accuracy of Claims-Based Risk Scoring Models", Society of Actuaries, Oct. 2016, pp. 1-90.

McCarthy, et al., "The Estimation of Sensitivity and Specificity of Clustered Binary Data", Statistics and Data Analysis, SUGI 31, Paper 206-31, 10 pages.

Mojsilovic, et al., "Semantic based categorization, browsing and retrieval in medical image databases", Proceedings of the International Conference on Image Processing, IEEE, 2002, pp. 145-148., 2002.

Pearson, et al., "Disease Progression Modeling from Historical Clinical Databases", Proceedings of the Eleventh ACM SIGKDD International Conference on Knowledge Discovery in Data Mining, Aug. 21-24, 2005, pp. 788-793.

Ribeiro, "Why Should I Trust You?", Explaining the Predictions of Any Classifier, Feb. 16, 2016, 10 Pages.

Schneider, "Enabling Advanced Analytics to Improve Outcomes", Truven Health Analytics, Aug. 23, 2012, pp. 1-46, Aug. 23, 2012, 46.

Shen, "Using Cluster Analysis, Cluster Validation, and Consensus Clustering to Identify Subtypes of Pervasive Developmental Disorders", Nov. 2007, 119 pages, Nov. 2007, 119 pages.

Soni, et al., "Using Associative Classifiers for Predictive Analysis in Health Care Data Mining", International Journal of Computer Applications (0975-8887), vol. 4, No. 5, Jul. 2010, pp. 33-37.

Su, et al., "Using Bayesian Networks to Discover Relations Between Genes, Environment, and Disease", BioData http://www.biodatamining. org/content/6/1/6, 2013 (Year: 2013), 21 Pages.

Suo, et al., "Risk Factor Analysis Based on Deep Learning Models", Proceedings of the 7th ACM International Conference on Bioinformatics, Computational Biology, and Health Informatics, Oct. 2-5, 2016, 10 Pages.

Tan, et al., "Cluster Analysis: Basic Concepts and Algorithms,", Introduction to Data Mining (Second Edition), Chapter 8, Feb. 2018, pp. 487-568, Feb. 2018, 82.

Truven Health Analytics, "Flexible Analytics for Provider Evaluation", Solution Spotlight, 2017, 4 Pages.

Truven Health Analytics, "Modeling Studies: Published Articles and Presentations", 2016, pp. 1-6.

Truven Health Groups, "Enterprise Decision Support", Product Spotlight, 2012, 2 Pages.

U.S. Patent and Trademark Office, "Final Office Action Received", U.S. Appl. No. 15/465,542, Jan. 4, 2022 60 pages.

U.S. Patent and Trademark Office, "Final Office Action Received", U.S. Appl. No. 15/465,542, Dec. 30, 2019, 54 Pages.

U.S. Patent and Trademark Office, "Final Office Action Received", U.S. Appl. No. 15/465,550, Mar. 21, 2022, 12 Pages.

U.S. Patent and Trademark Office, "Final Office Action Received", U.S. Appl. No. 15/927,766, Oct. 6, 2020, 22 Pages.

U.S. Patent and Trademark Office, "Final Office Action Received", U.S. Appl. No. 15/465,550, Oct. 14, 2020, 15 Pages.

U.S. Patent and Trademark Office, "Non Final Office Action Received", U.S. Appl. No. 16/386,123, Jun. 28, 2022, 55 Pages.

U.S. Patent and Trademark Office, "Non Final Office Action Received", U.S. Appl. No. 15/927,766, Apr. 30, 2020, 19 Pages.

U.S. Patent and Trademark Office, "Non Final Office Action Received", U.S. Appl. No. 15/465,550, Jun. 26, 2019, 8 Pages.

U.S. Patent and Trademark Office, "Non Final Office Action Received", U.S. Appl. No. 15/465,550, Mar. 13, 2020, 12 Pages.

U.S. Patent and Trademark Office, "Non Final Office Action Received", U.S. Appl. No. 15/465,542, Mar. 19, 2019, 29 Pages.

U.S. Patent and Trademark Office, "Non-Final Office Action Received", U.S. Appl. No. 15/465,542, Apr. 1, 2021, 73 Pages.

U.S. Patent and Trademark Office, "Non-Final Office Action Received", U.S. Appl. No. 15/465,550, Jul. 29, 2021, 31 Pages.

U.S. Patent and Trademark Office, "Non-Final Office Action Received", U.S. Appl. No. 16/724,264, Mar. 21, 2022, 20 Pages.

U.S. Patent and Trademark Office, "Notice of Allowance Received", U.S. Appl. No. 15/927,766, Oct. 14, 2021, 35 Pages.

U.S. Patent and Trademark Office, "Restriction Requirement Received", U.S. Appl. No. 16/724,264, Oct. 7, 2021, 6 Pages.

U.S. Patent and Trademark Office, "Notice of Allowance Received", U.S. Appl. No. 15/465,550, Aug. 16, 2022, 8 Pages.

U.S. Patent and Trademark Office, "Notice of Allowance Received", U.S. Appl. No. 15/465,542, Aug. 24, 2022, 11 Pages.

Bodhe, et al., "A Proposed Mobile Based Health Care System for Patient Diagnosis using Android OS," International Journal of Computer Science and Mobile Computing, vol. 3 Issue.5, May 2014, p. 422-427 (Year: 2014).

U.S. Patent and Trademark Office, "Notice of Allowance Received", U.S. Appl. No. 15/465,542, Oct. 28, 2022, 12 Pages.

U.S. Patent and Trademark Office, "Final Office Action Received", U.S. Appl. No. 16/724,264, Nov. 30, 2022, 11 Pages.

U.S. Patent and Trademark Office , "Final Office Action Received", U.S. Appl. No. 18/414,296, Jul. 10, 2024, 11 Pages.

U.S. Patent and Trademark Office , "Non-Final Office Action Received", U.S. Appl. No. 18/414,296, Mar. 22, 2024, 13 Pages.

U.S. Patent and Trademark Office , "Non-Final Office Action Received", U.S. Appl. No. 18/169,372, May 8, 2024, 16 Pages.

U.S. Patent and Trademark Office , "Non-Final Office Action Received", U.S. Appl. No. 18/596,720, Sep. 16, 2024, 37 Pages.

U.S. Patent and Trademark Office , "Notice of Allowability Received", U.S. Appl. No. 18/169,372, Oct. 16, 2024, 2 Pages.

U.S. Patent and Trademark Office , "Notice of Allowance Received", U.S. Appl. No. 16/386,123, Dec. 13, 2023, 12 Pages.

U.S. Patent and Trademark Office , "Notice of Allowance Received", U.S. Appl. No. 18/169,363, Mar. 27, 2024, 10 Pages.

U.S. Patent and Trademark Office , "Notice of Allowance Received", U.S. Appl. No. 18/169,372, Sep. 25, 2024, 9 Pages.

Voshaar , et al., "Calibration of the PROMIS Physical Function Item Bank in Dutch Patients with Rheumatoid Arthritis", PLOS ONE, vol. 9, Issue 3, Mar. 2014, pp. 1-11.

Zhong, Yizhen , et al., "Characterizing Design Patterns of EHR-Driven Phenotype Extraction Algorithms", In 2018 IEEE International Conference on Bioinformatics and Biomedicine (BIBM), Madrid, Spain, 2018; doi: 10.1109/BIBM.2018.8621240, pp. 1143-1146.

(56)         References Cited

OTHER PUBLICATIONS

U.S. Appl. No. 19/192,428, Non-Final Office Action mailed on Feb. 3, 2026, 37 pages.

* cited by examiner

Process health care information to generate additional data
300

Specify training set(s) of patient data
302

Train classifier(s)
304

Apply classifier(s) to patient data, returning probabilities
306

Store computed probabilities as part of patient data
308

Compare probability to a threshold
310

Automatically enroll patient in program
312

Add structured data filed to patient record
314

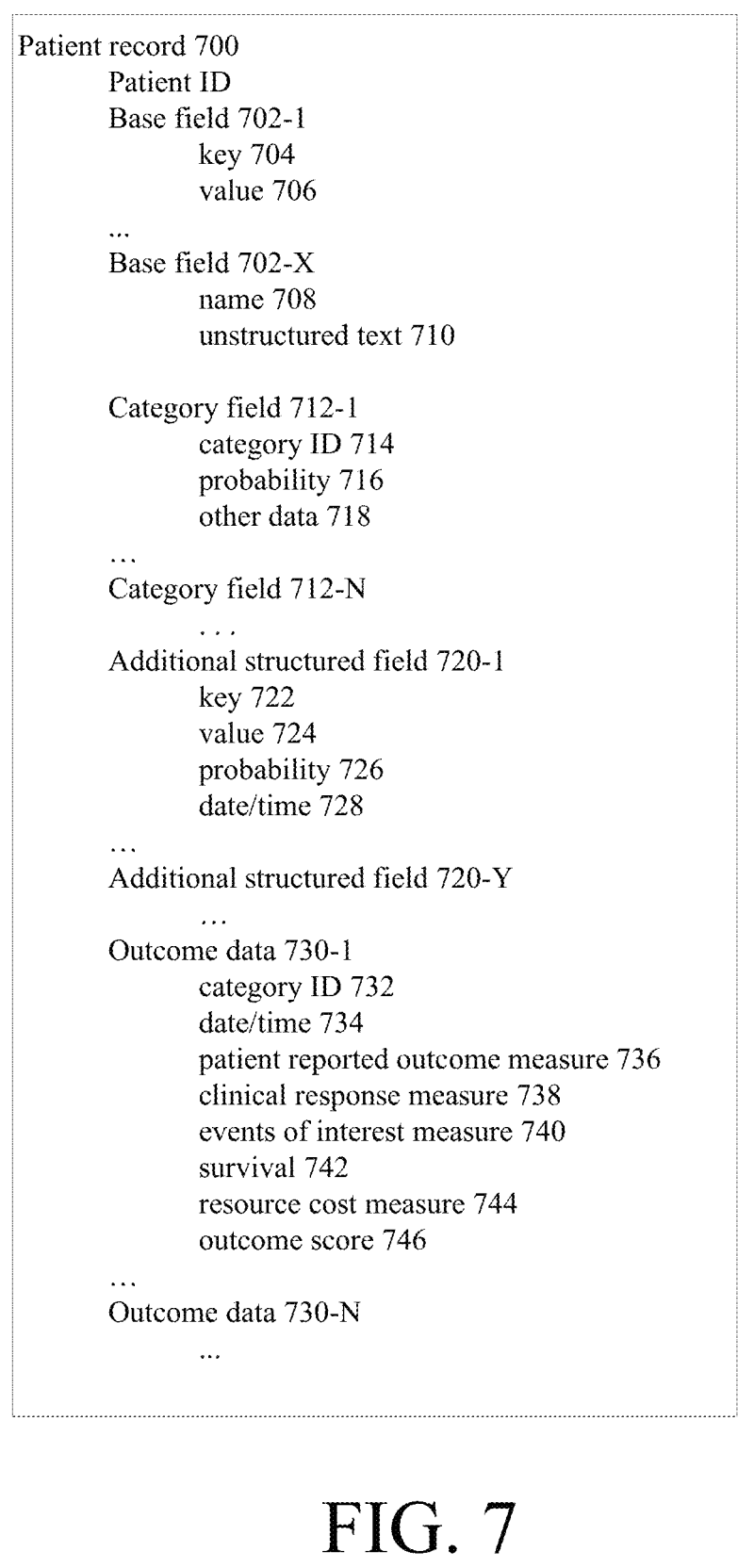

Patient record 700
    Patient ID
    Base field 702-1
        key 704
        value 706
    ...
    Base field 702-X
        name 708
        unstructured text 710

Category field 712-1
        category ID 714
        probability 716
        other data 718
    ...
    Category field 712-N
        . . .
    Additional structured field 720-1
        key 722
        value 724
        probability 726
        date/time 728
    ...
    Additional structured field 720-Y
        ...
    Outcome data 730-1
        category ID 732
        date/time 734
        patient reported outcome measure 736
        clinical response measure 738
        events of interest measure 740
        survival 742
        resource cost measure 744
        outcome score 746
    ...
    Outcome data 730-N
        ...

FIG. 7

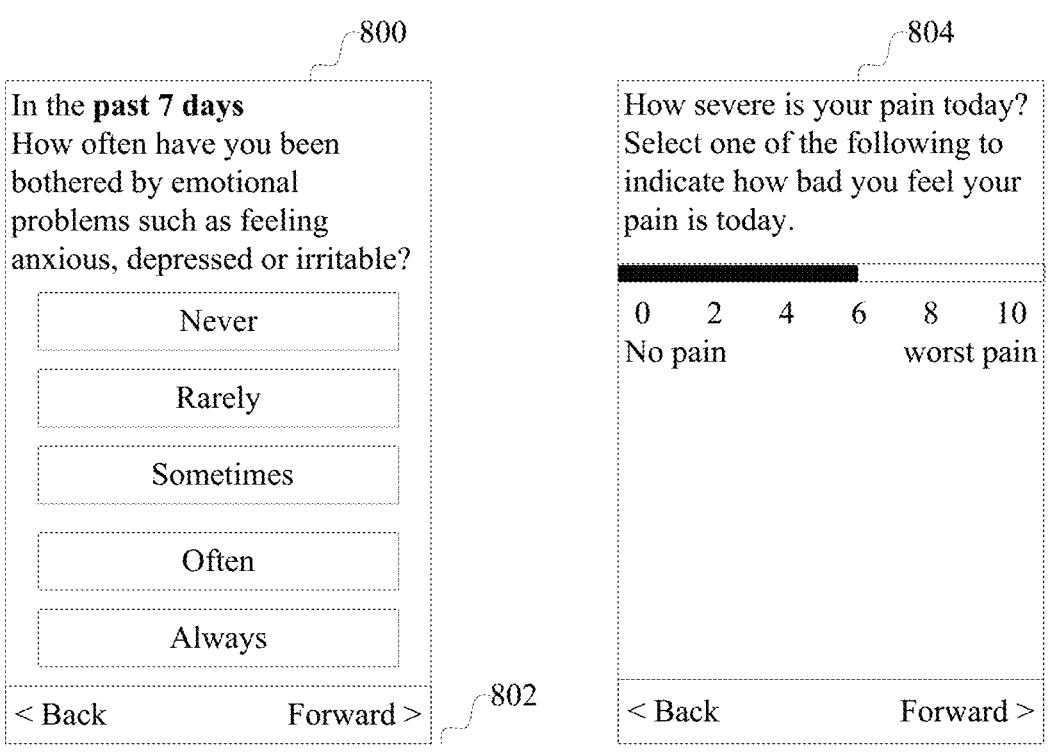
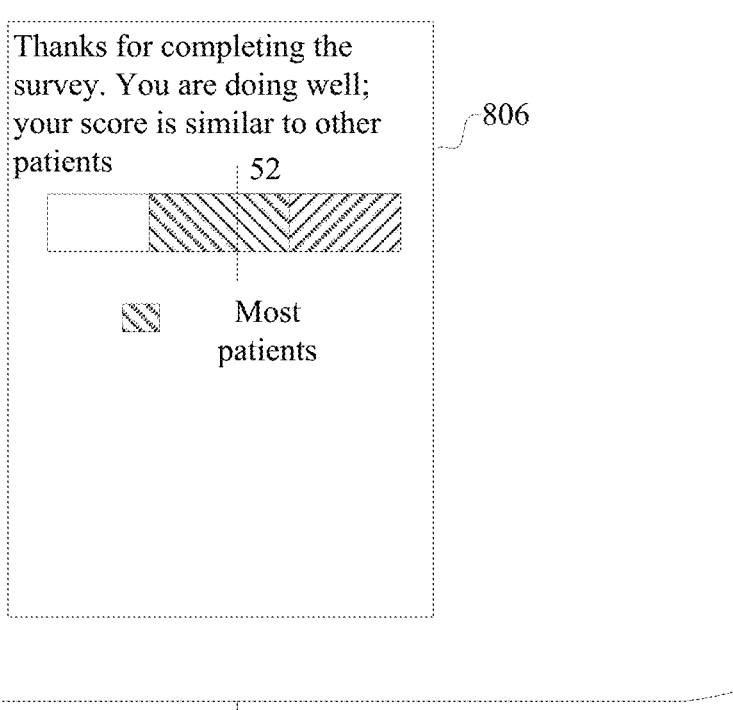
FIG. 8

Thanks for completing the survey!

Up 24 since Dec. 31, 2015

My Programs
Hospital Network

Show:   Percentage Active           6 month trailing average

Cardiology Progam       1500
4 Modules

45%          89%          78%

Ischemic Heart Disease    Hypertensive Heart...    Valvular Heart Disease
152 Active Patients       1239 Active Patients    1349 Active Patients

Comparison Report
Change in Aggregate Outcomes Scores from Baseline

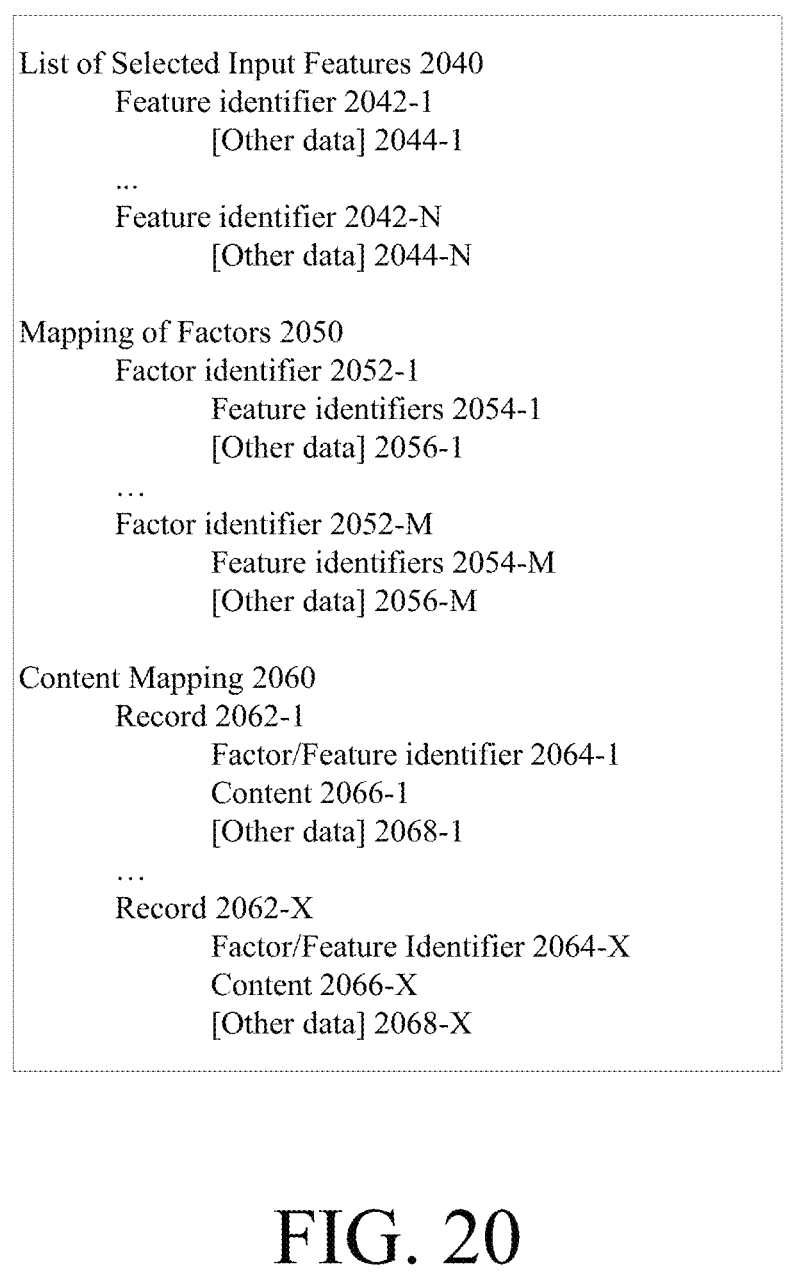

[x] Risk Adjusted Scores                    Include data from: Current year to date List of Selected Input Features 2040
         Feature identifier 2042-1
                 [Other data] 2044-1

...

Feature identifier 2042-N
                 [Other data] 2044-N

Mapping of Factors 2050
         Factor identifier 2052-1
                 Feature identifiers 2054-1
                 [Other data] 2056-1

...

Factor identifier 2052-M
                 Feature identifiers 2054-M
                 [Other data] 2056-M Content Mapping 2060
         Record 2062-1
                 Factor/Feature identifier 2064-1
                 Content 2066-1
                 [Other data] 2068-1

...

Record 2062-X
                 Factor/Feature Identifier 2064-X
                 Content 2066-X
                 [Other data] 2068-X

FIG. 20

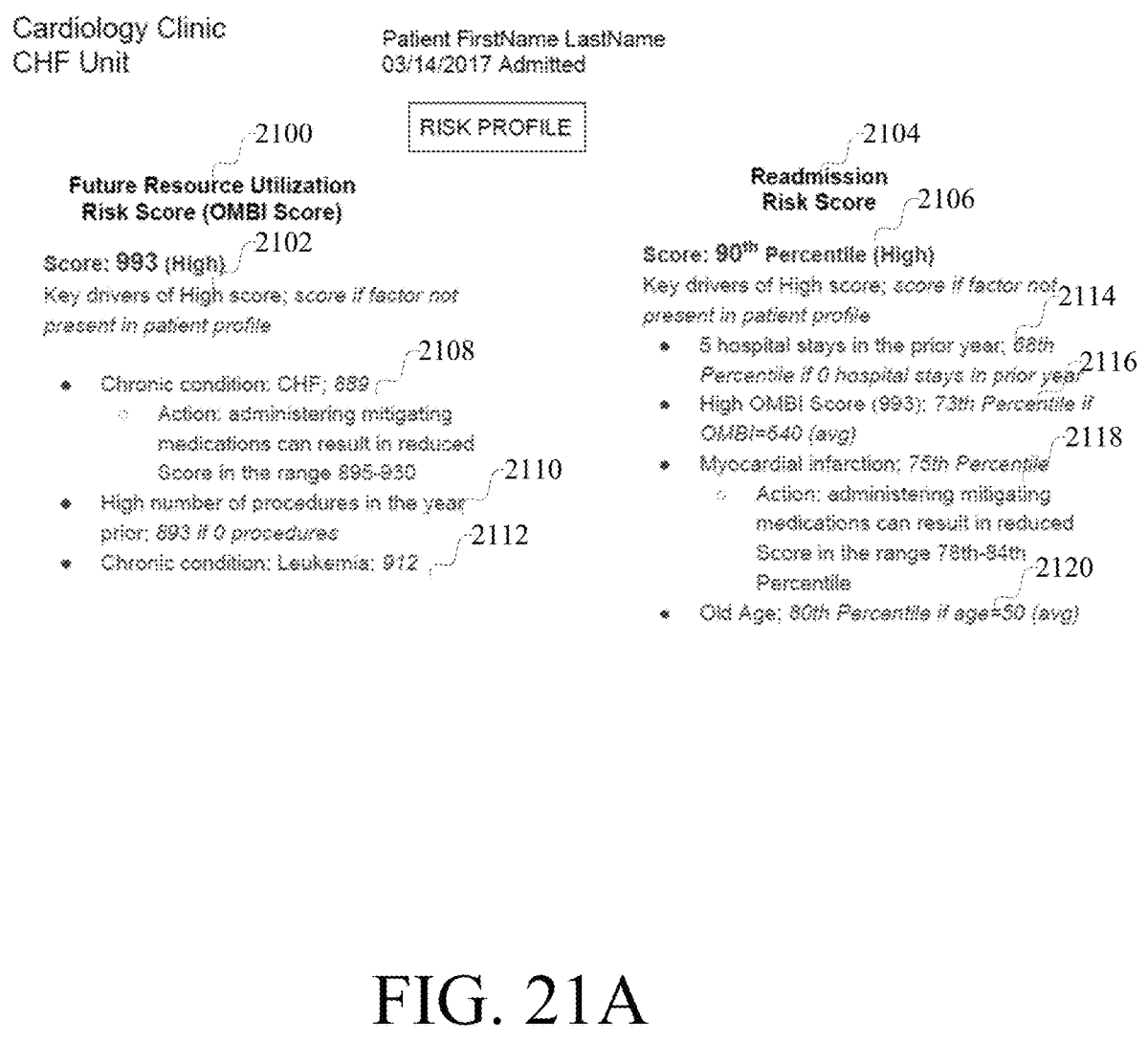

Cardiology Clinic
CHF Unit

Patient FirstName LastName
03/14/2017 Admitted

RISK PROFILE

**Future Resource Utilization
Risk Score (OMBI Score)** ⌐2100

Score: 993 (High) ⌐2102

Key drivers of High score; score *if factor not
present in patient profile*

- Chronic condition: CHF; *889* ⌐2108
  - Action: administering mitigating
    medications can result in reduced
    Score in the range *895-930* ⌐2110
- High number of procedures in the year
  prior; *893 if 0 procedures* ⌐2112
- Chronic condition: Leukemia; *912*

**Readmission
Risk Score** ⌐2104 ⌐2106

Score: 90th Percentile (High)

Key drivers of High score; score *if factor not
present in patient profile* ⌐2114

- 5 hospital stays in the prior year; *66th
  Percentile if 0 hospital stays in prior year* ⌐2116
- High OMBI Score (993); *73th Percentile if
  OMBI=640 (avg)* ⌐2118
- Myocardial infarction; *75th Percentile*
  - Action: administering mitigating
    medications can result in reduced
    Score in the range *78th-84th
    Percentile* ⌐2120
- Old Age; *80th Percentile if age=50 (avg)*

FIG. 21A

How will knee surgery affect my overall quality of life?

2130

74%
of patients like you
IMPROVE after surgery in
overall quality of life

Chance of
NO CHANGE

Chance of
GETTING WORSE

DAILY LIFE FUNCTION

RISE FROM BED    STAND    CLIMB STAIRS    CARRY HEAVY OBJECTS

2132

Right now, you have ____ difficulty with daily life functions.

2138

With surgery, you'll have a ____ chance of IMPROVEMENT in your daily life functions.

RECREATIONAL ACTIVITIES

2144

Update your modifiable risk factors to see how your outcomes can further improve

FIG. 21B

INFORMATION SYSTEM PROVIDING EXPLANATION OF MODELS

CROSS-REFERENCE TO RELATED APPLICATIONS

This application is a non-provisional application of prior-filed provisional patent application Ser. No. 62/474,587, entitled "Health Care Information System Providing Explanations of Classifiers of Patient Risk", filed Mar. 21, 2017, which is hereby incorporated by reference.

BACKGROUND

A challenge in the health care industry is providing meaningful data, on a regular basis, to health care providers, patients, insurers, care managers and other entities, regarding health care outcomes of patients, quality of care by health care providers, and a variety of other health-related metrics. Recently, computer systems have been able to provide measures of health care outcomes and other health-related metrics, such as various types of outcome measurements, scores, categorization and classification, risk identification, and risk factors, for patients, and quality of care and other metrics about health care providers. Such computer systems generally use models which perform analytical computations on patient data, which include, but are not limited to, mathematical operations applied to data, classifiers, clustering algorithms, predictive models, neural networks, deep learning algorithms and systems, artificial intelligence systems, machine learning algorithms, Bayesian systems, natural language processing, or other types of analytical models applied to small or large sets of data. Generally, such a model receives data values for an entity for a plurality of input features, and provides an output for the entity based on the received data values. Such models typically are trained using a training data set in which the outputs corresponding to a set of inputs is known.

Such models are complex, are typically non-linear, and generally do not provide sufficient direct information to indicate what input data most affects the output of the model. Without such information, it is difficult to explain and use the output of such models, whether for gaining deeper understanding of the degree to which the different components of entity data affect the output of the model, evaluating possible interventions for a patient with respect to such intervention's effect on the model output, predicting risk, analyzing quality of care, or for other uses.

SUMMARY

This Summary introduces a selection of concepts, in simplified form, which are described further in the Detailed Description below. This Summary is intended neither to identify key or essential features, nor to limit the scope, of the claimed subject matter.

A health care information system generates information that describes how different inputs to a model affect the output of the model, by creating a localized model for a given entity, and determining how the output of the localized model for the given entity changes in response to different inputs. The localized model is an approximation of the model which may or may not differ from the model.

This technique can be used for different types of models, such as models that classifies patients into categories or conditions, models that compute risk factors associated with patients, models that predict outcomes for patients, models that compute factor scores or outcome scores for patients, models that evaluate provider performance, models that predict costs, models that compute data values for fields with missing data, models that compute data values for quantities that are estimated based on other data, and yet other models that perform other analyses on health care information. In many cases, the model is trained using supervised machine learning techniques and is a type of machine learning model for which the behavior typically is nonlinear. This technique can be applied to computer models that process other types of data, and is not limited to health care information or the specific types of models described herein.

The computer system builds a localized model for a given entity based on the model and on data values for the given entity. The computer system inputs one or more different data values for selected input features of the localized model, while data values for the remaining input features of the localized model are fixed to data values for the given entity. In one implementation, the localized model is created by setting the data values for a set of the input features of the model, other than the selected input features, to data values for those input features for the given entity. In one implementation, the localized model is created by generating another, local model for the given entity, based on the model and on the data values for the given entity.

The selected input features can be selected from among input features of the model which correspond to explainable factors for the model. An explainable factor is a factor for which variation in values for corresponding input features of the model may have a relevant effect on the output of the model. The computer system described herein assesses the extent of the effect. Such factors may be selected, for example, based on known expected effect on the output of the model, or based on known importance of the factor without prior knowledge of expected effect on the output of the model, or for any other reason. For example, in health care systems, factors that are known to affect risk or that are medically important may be selected as explainable factors. Data representing the set of selected input features can be stored in a data structure in a library for use for multiple entities. For each of the selected input features, the library also can store one or more respective different data values to be used in analyzing localized models for entities.

The set of selected input features, or explainable factors, further can correspond to actions which can be performed with respect to the given entity, such as a particular treatment or behavior change for a patient. This kind of explainable factor is called an actionable factor herein. A set of actionable factors also can be stored in the library, representing actions which can be performed with respect to the given entity, wherein the library stores a mapping between each actionable factor and one or more respective input features in the set of selected input features. The actionable factors can be medically modifiable factors. A medically modifiable factor is a factor, such as a treatment, intervention or other factor that can be acted upon with respect to a patient, under direction of a health care provider. Typically such a factor can be a treatment, such as a dosage of a medication, and an expected change in patient data due to the treatment, such as a measured laboratory result. The library further can include, for each actionable factor in the set of actionable factors, human-understandable content describing the actions which can be performed with respect to the given entity.

The computer system performs a sensitivity analysis on the localized model for the given entity. Sensitivity analysis, as used herein, refers to applying a different data value for a selected input feature to the localized model, in response to which the localized model for a given entity provides an output, as a way of evaluating what the result of the model would be if the data value for the given entity for the selected input feature were different. In one implementation, the computer system applies one or more different data values to the set of selected input features of the localized model for the given entity, while data values for the remaining input features of the localized model are fixed to data values for the given entity. In some implementations, there may be a single different data value for one of the selected input features, in response to which the localized model provides an output indicating what the result of the model would be if the data value for the given entity for the one of the selected input features were different. In some implementations, a sensitivity analysis of the localized model with respect to the selected input features can be performed, for example, by using linear regression, nonlinear regression, or Bayesian sensitivity analysis, or other types of analysis.

The results of the sensitivity analysis performed on this localized model for the given entity indicate which of the selected input features or factors, whether explainable, actionable or medically modifiable, which were not fixed based on the data for the given entity, have the most impact on the output of the model for that entity. The system can rank the selected input features or factors, in order of impact on the result from the model for the given entity, based on the output of the sensitivity analysis performed on the localized model for that entity. It is possible that different features or factors may be identified as having the most impact for respective different entities.

In the following Detailed Description, reference is made to the accompanying drawings which form a part of this disclosure. These drawings show, by way of illustration, example implementations. Other implementations can be made without departing from the scope of this disclosure.

BRIEF DESCRIPTION OF THE DRAWINGS

FIG. 7 is an illustrative example implementation of data structures.

FIG. 8 are example graphical user interfaces for use on a client computer for patient entry of patient reported outcomes.

FIG. 20 is an illustrative example of data structures.

FIGS. 21A-21F are illustrative examples of a graphical user interface.

DETAILED DESCRIPTION

Figure 1:
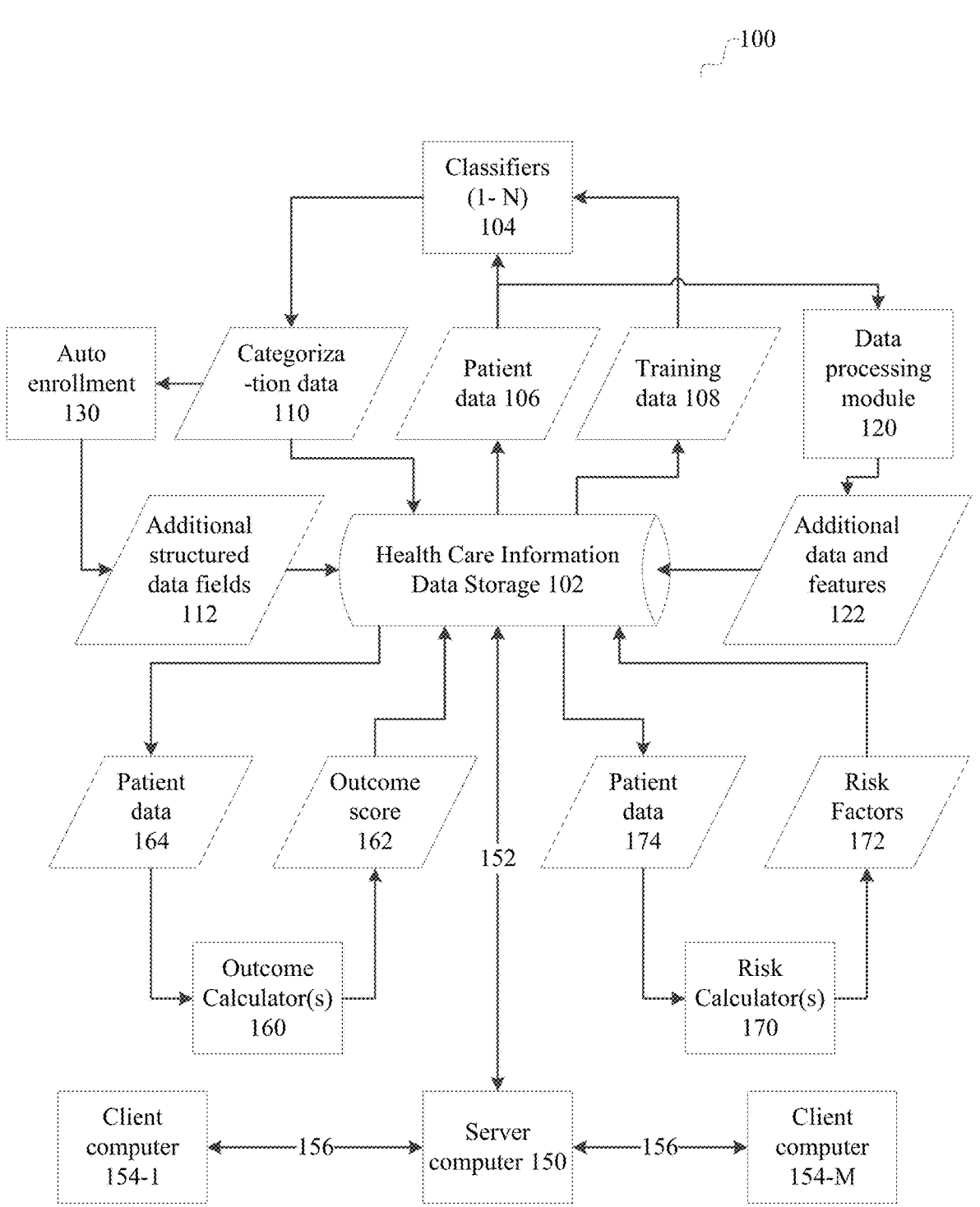
FIG. 1 is a block diagram of an example computer system supporting a health care information system providing standardized outcome scores across patients.

Referring to FIG. 1, a block diagram of an example implementation of a computer system supporting a health care information system will now be described. A detailed example implementation of such a health care information system is provided by FIGS. 1-17. The kinds of models used in this health care information system, such as for categorization or classification of patients, computation of factor scores and outcome scores, assessment of risk and risk factors, and other models, can be explained using the techniques described in more detail below in connection with FIGS. 18-21.

A computer system 100 as shown in FIG. 1 includes health care information data storage 102 which stores health care information for a plurality of patients. The health care information for a patient can be obtained from a number of different sources of health care information for the patient including electronic medical records from the patient's health care providers, insurance providers and other sources.

More particularly, health care information can include, but is not limited to, information recorded for patients by a health care provider. Examples of health care providers include, but are not limited to, individuals, such as a physician, a therapist, a nurse, or support staff, and organizations, such a hospital or other facility employing health care providers. Health care information can include information from entities other than health care providers but who are otherwise involved in health care, such as insurers, laboratories, supply providers and the like, which may store information about claims, diagnostic tests, laboratory work, supplies and vendors. Health care information can include information reported by patients and/or their caregivers.

Such health care information generally includes demographic information and medical information.

The demographic information can include, for example, age, gender, race, family history, social history, and other information for the patient. If personally identified information authorized and stored, such information can include a name, an address and various contact information.

The medical information can include, for example, information about reported or observed symptoms of the patient, diagnoses made by the health care provider, any medications, treatments and other interventions prescribed or recommended by the health care provider, and/or any requests for laboratory work or diagnostic tests, and related reports or results. Such data can be stored as a history of interactions with the health care provider and may have multiple instances of a type of data over time, such as vital signs and lab results. Such data typically includes information, typically representing symptoms, diagnoses, procedures and medications, which is typically coded according to a standard, such as ICD-9, ICD-10, CPT, SNOMED, LOINC, COSTAR, and RxNorm coding systems.

Such health care information can be de-identified data such that any personally identifying information is removed, in which case the health care information for a patient is associated with a unique code representing that patient, which code distinguishes the patient from other patients.

Such health care information generally includes both structured and unstructured data. Structured data generally is data that has a specified data model or other organization, whereas unstructured data generally does not. By way of example, structured data can include database records, attribute-value pairs, and the like, whereas unstructured data can be either textual data, such as free text, documents, reports of results, published and unpublished literature, and the like, or non-textual data, such as image data of which DICOM data is an example.

Health care information also can include cost information related to resources for various activities related to providing health care for a patient. Thus, for each activity performed with respect to a patient, resource utilization information also can be made available. Resources can include personnel, equipment, supplies, space, and the like. Resources generally have an associated cost, typically represented by a cost per unit, cost per unit of time, cost per unit of space, and the like.

The data storage 102 that stores such health care information can include a database, such as a relational, object-oriented, or other structured database, such as a structured data file that stores data in columns, optionally in key-value pairs. The database can be stored on a computer, such as described below in FIG. 6, that is configured to allow access to the health care information by other computers through defined transactions. The computer also can be programmed to perform database operations on the database as part of such transactions. Such a computer supporting the database is configured with sufficient processors, memory and storage to support storage of data in, and access to that data from, data storage 102.

The data storage 102 can include data from multiple storage systems (not shown) for each of multiple entities. While data from multiple entities can remain stored in their respective storage systems, such data can be consolidated in data storage 102. Multiple storage systems of multiple entities typically are distributed geographically, so such consolidation generally occurs by periodic requests for transmission of data over one or more computer networks (not shown) to the data storage 102.

The computer system includes a plurality of classifiers 104 (104-1 to 104-N, hereinafter individually or collectively "104"). Classifiers generally are implemented on one or more general purpose computers, such as described below in connection with FIG. 6, programmed by one or more computer programs to implement a classification process.

The classifiers 104 process patient data 106 from the health care information data storage 102 related to patients to determine a likelihood that a patient belongs in a category.

A classifier 104 is defined for each category, thus providing N different classifiers for N different categories. A category can be associated with a medical condition or procedure and an outcome function with which outcome scores are to be measured and tracked for patients in that category.

The health care information system can include a training process that implements machine learning techniques to train the classifiers 104 given training data 108, including data for a set of patients. In some implementations, trained classifiers can be used. In some implementations, and for some categories, a classifier can be a simple rule applied to the patient data. For example, whether a patient has received a specific surgical procedure can be determined without a trained classifier. After training, a trained classifier 104 applied to patient data 106 for a patient determines a likelihood that the patient has a condition corresponding to the classifier, indicated as categorization data 110 in FIG. 1. For each classifier, the health care information data storage 102 can store categorization data 110 over time for each patient, indicating whether the patient is likely in the category represented by the classifier.

A classifier 104 can be built using any of family of algorithms described as supervised classification or machine learning or econometrics algorithms, which perform functions such as classification, prediction, regression or clustering. With such algorithms, a computer generates a model based on examples provided in a training set. Any supervised classification or machine learning model can be used as a classifier, such as support vector machines, conditional random fields, random forest, logistic regression, decision tree, maximum entropy, artificial neural networks, genetic algorithms, or other classifier or predictive model, or combination of such models, for which parameters of a function can be trained by minimizing errors using a set of training examples. Such models generally produce a score, which can be indicative of a classification or prediction, and a probability. In some cases the score and probability are one and the same value.

One or more additional data fields 112 can be associated with a category. For example, if the category is associated with a specific health program, then the additional data fields can include any data fields for which data is collected as part of that health program. After a patient is classified in a category, the health care information system adds the data fields for that category to the patient record. These additional data fields can be structured to store a value and a probability indicative of a level of certainty about that value. The health care information system can populate these additional data fields with values and probabilities for those values in a number of ways. For example, the health care information system can derive values for the additional data fields for a patient from existing health care information for the patient, using a data processing module 120 described in more detail below. As another example, a health care information system can prompt users to enter data, such as forms to be completed by patients or their health care providers. The health care information system can be configured to derive values for these fields probabilistically, using one or more classifiers, which in turn provides both a value and a probability associated with that value to be stored in the additional data fields.

The category in which a patient is classified may be associated with a health program, such as a health outcomes measurement program, or a clinical program, or a clinical trial, or a clinical study, or a clinical care program or a treatment program. If the probability that a patient is classified in a category exceeds a threshold, then the health care information system can initiate an automatic enrollment process 130 to enroll the patient in any health program associated with that category. In some instances, the additional data fields 112 added to the patient data are specified by the health program, and the automatic enrollment process adds these data fields to the patient record. The automatic enrollment process also can specify data entry forms to be presented to the patient on a regular basis to provide for further systematic data collection.

The health care information system also includes an outcome function for each category for computing an outcome score for patients in that category. The outcome function for a condition for a patient is a weighted function of one or more scores based on one or more factors, such as patient and/or caregiver reported outcomes, clinical response measures, survival, events of interest and resource consumption. That is, given a score for one or more factors for a condition for a patient, based on that patient's data, the health care information system computes a weighted function of these scores to compute the outcome score. The set of weights used to compute the outcome score for a condition for a patient is the same across all patients with the same condition. The health care information system can be programmed to allow the set of weights to be changed to allow for analysis of how outcome scores are affected by different weights.

The health care information system includes an outcome calculator 160 that periodically computes an outcome score 162 for each patient, for each condition which the patient has, i.e., for each category in which that patient is classified, using the patient data 164. At any given time point in an historical patient record, the health care information system can compute an outcome score for the condition for the patient. The health care information system can compute the outcome score for a condition for a patient at many points in time, over time. A patient can have multiple conditions for which the health care information system separately computes separate outcome scores 162.

The computer system can include a data processing module 120 that performs various processing on the patient data 106 stored in the data storage 102, so as to convert patient data into additional data and features 122. Such additional data and features can be used, for example, by the classifiers 104, or other components of the computer system. The data processing module 120 also can be implemented using a general purpose computer such as described in FIG. 6 and programmed to perform such processing.

For example, the data processing module can populate the additional data fields 112 for a category, or any other data field missing a value, with values, and optionally probabilities for those values, in a number of ways. For example, the health care information system can derive values for the additional data fields for a patient from existing health care information for the patient. A function can be associated with the data field to define how to derive the value for the data field as a function of other patient data. As another example, the data processing module can prompt a user to enter data, such as by presenting a form to be completed by a patient or a health care provider. The data processing module can derive values for these fields probabilistically, using one or more classifiers, which in turn provides both a value and a probability associated with that value to be stored in the data fields. The data processing module can identify similar patients, and generate a value for a data field based on values stored for similar patients.

The data processing module can apply natural language processing techniques to patient data to generate additional features, such as for training classifiers. The data processing module can perform various normalization or filtering operations to ensure data is consistent across records and with a patient record.

The data processing module also can process patient data using a variety of techniques, such as deep learning models, to identify pertinent features in the patient data. In such an implementation, the patient data is represented as a temporal matrix in which one axis is time and another axis is fields of patient data. The fields can be all of the patient data fields, or selected patient fields. This temporal matrix is processed to identify temporal patterns found across patients within a data field or across combinations of data fields. Such temporal patterns can be identified using a variety of techniques, such as image processing, image pattern recognition, matrix convolution, neural networks. The results of such processing can be used to define features for training and applying classifiers, whether for categorizing patients and/or for calculating risk factors. The identified features can be added as data fields in the patient data.

In some implementations, the data in a field can be represented in the temporal matrix as a transition in state occurring at a point in time. For example, a patient may have a diagnosis of diabetes. While a diagnostic code may arise in the patient data record at a point in time, this characteristic of the patient for the purposes of creating the temporal matrix for deep learning analysis can be represented as a first state (non-diabetic), which transitions to a second state (diabetic) at the point in time corresponding to the diagnosis.

Other techniques of extracting features from a temporal matrix constructed from patient data can be used. For example, an approach as described in "Risk Prediction with Electronic Health Records: A Deep Learning Approach", by Cheng, Y., Wang, F., Zhang, P., Hu, J., *in SIAM International Conference on Data Mining (SDM)*, 2016. can be used.

A particular kind of data processing useful to analyzing health care outcomes for patients is the determination of risk factors for those patients, such as a risk of readmission to a hospital, risk of complications due to surgery and the like. The health care information system also can include risk calculators 170 that compute such risk factors 172 in view of patient data 174.

Risk calculators 170 also can be built using any of family of algorithms described as supervised classification or machine learning or econometrics algorithms, which perform functions such as classification, prediction, regression or clustering. With such algorithms, a computer generates a model based on examples provided in a training set. Any supervised classification or machine learning model can be used as a classifier, such as support vector machines, conditional random fields, random forest, logistic regression, decision tree, maximum entropy, artificial neural networks, genetic algorithms, or other classifier or predictive model, or combination of such models, for which parameters of a function can be trained by minimizing errors using a set of training examples. Such models generally produce a score, which can be indicative of a classification or prediction, and a probability. In some cases, the score and the probability are one and the same value. For a risk calculator, this score and/or probability may be associated to the risk or likelihood of a future outcome or to the likelihood that the patient belongs to a certain cohort by disease type or disease severity.

A risk calculator can be associated with a category into which patients are classified. Thus, a risk factor associated with a category can be calculated for each patient classified in that category. The calculated risk factors can be stored as additional data fields for that category, and can include probabilities related to the risk factors.

The health care information data storage 102 can include a server computer (not shown) implemented using a general purpose computer such as described below in connection with FIG. 6 to control the execution of operations by the classifiers 104, auto enrollment 130, data processing module 120, outcome calculator(s) 160 and risk calculator(s) 170. Each of these components can have its own application programming interface (API) implementing a service oriented architecture. An API can be implemented that provides security, such as via SSL/TLS encryption with user authentication. Programs execution by the health care information data storage 102 can schedule and control processing performed by the other components. Patient data 106 can be processed by such components periodically in batch jobs, such as daily or weekly or other periodic execution.

The health care information data storage 102 also can be accessed through one or more server computers 150 over a computer network 152 through an application programming interface. While only one server computer 106 is shown in FIG. 1, configurations of multiple server computers also can be used. In the example shown in FIG. 1, a plurality of client computers 154-1, . . . , 154-M, (hereinafter "154") communicate with one or more server computers 150 by connecting to a computer network 156 and transmitting messages to, and receiving messages from, the server computer 150 using a communication protocol over the computer network 156.

The one or more server computers 150 can be implemented using a general purpose computer such as described below in connection with FIG. 6. The general purpose computer is configured as a server computer, with sufficient processors, memory, storage and communication connections. In one example implementation, the server computer can be configured to operate as a "Web" server, or a server computer that implements a hypertext transfer protocol (HTTP) or secure hypertext transfer protocol (HTTPS), using a computer program such as the Apache web server computer program or other similar web server computer programs. Using an HTTPS server implementation, users can login with secure connections and have permissions associated with their user sessions which in turn can be used by the one or more server computers 150 to provide a personalized user experience for each user and to ensure each user accesses only those data records in storage 102 for which the user has authorization. For example, a patient is limited to accessing that patient's own records. A health care provider is limited to accessing only patient data for its patients. Access control by roles within a health care provider, for example a doctor may have access to more patient data than someone in an administrative role, also may be provided.

The computer networks can be any type of computer network that allows computers to communicate messages with each other. An example computer network is an Ethernet network, which supports local and wide area networks, and which can support communications using an internet protocol (IP). The computer network can be public (such as the internet) or private (such as a private network supporting IP). Multiple types of networks may be involved in connecting the one or more client computers 154 to the one or more server computers 150.

The client computers 154 can be any kind of computer, generally in the form of a general purpose computer such as described below in connection with FIG. 6. For example, the client computer can be a desktop computer, laptop or notebook computer, or mobile computing device such as a smartphone, tablet computer, handheld computer and the like.

In one example implementation, a client computer 154 is configured with a computer program called a "web" browser application which implements both communication protocols and rendering conventions for exchanging information with "web" server computers. Such a browser application generally allows the client computer to communicate with a server computer over a computer network using HTTP, HTTPS or similar communication protocol, and renders and displays documents received in a markup language or other standardized format supported by the browser application. Example browser applications include, but are not limited to, the Firefox, Chrome, Safari, Internet Explorer browser applications. In another example implementation, a client computer can be configured with a dedicated computer program, or application, that is designed to interact primarily with the one or more server computers 150.

Through a client computer 154, various operations with respect to the health care information stored in data storage 102 can be provided by the server computer 150 to end users.

For example, a client computer 154 can present a graphical user interface that presents, for each patient, the outcome score for a selected condition for the patient, whether at a current point in time, a past point in time or over a period of time. The graphical user interface can present information about how the outcome score is computed, based on the weighting function and the underlying scores for the different factors.

Also, a client computer 154 can present a graphical user interface that presents forms for data entry, through which a user can enter data requested to populate the additional data fields for a patient based on the categories in which the patient has been classified. Such data entry forms can be presented to various users, such as care providers and patients, to provide, at least in part, the patient reported outcomes and clinical response measures used in computing outcome scores for patients.

The health care information system also can provide information about what patient data has the most impact on the outcome score, or on a factor score, or on a risk factor for that patient. Such information relates to explaining how classifiers generate the patient data, scores and risk factors. In one implementation, a locally interpretable model (not shown in FIG. 1, but described in more detail below in connection with FIG. 18) is built around a classifier. This model represents how medically modifiable factors would affect the outcome of the classifier. These medically modifiable factors are mapped to an associated set of suggested direct or indirect actions for the patient. These factors can be ranked in order of risk mitigation based on the model. Such data can be generated for each patient and stored as part of their patient data.

Turning now to FIG. 7, an illustrative example implementation of data structures stored in the health care information storage 102 will now be described. The example in FIG. 7 illustrates data for patient records pertinent to tracking and determining their health care outcomes as described herein. Other data sets, such as those providing demographic information, insurance information, provider information, and relationships among patient and providers, can be stored in other database structures using conventional techniques.

In FIG. 7, a patient record 700 has a patient identifier 701 and includes a number of base fields (702-1 to 702-X). These base fields can be structured, such as by having a key 704 and value 706, or unstructured, such as by having a name 708 and unstructured text field 710. Some of the structured data fields can be created by processing unstructured data; some missing data in structured data fields can be imputed by processing data from other fields, and similar data from similar patients. There can be a very large number of base fields 702.

The patient record 700 also can have a number of category fields 712-1 to 712-N which represent categories into which a patient can be classified. A category field can have an identifier 714 identifying the category and a value 716 indicating a likelihood that the patient is classified in that category. Other data 718 can be stored for the category, such as a name of a health program or condition associated with the category, model type and/or model name or other information about the classifier used to match the patient to this classifier and/or statistics obtained from applying that classifier to the patient. The other data 718 also can include information for tracking any schedule of patient data entry for patient record outcomes based on this category.

Next, if a patient is classified in a category, any additional data fields 720-1 to 720-Y for that category are added to the patient record. These additional data fields can be structured or unstructured data fields. For example, an additional data field can be in the form of a key 722, value 724 and probability 726 indicating a likelihood that the stored value 724 is correct. An additional data field may represent a risk factor to be computed for patients in that category. As another example, the additional data field can refer to or include image data. If an additional data field is specified by different categories, then that additional data field can be added only once to avoid redundancy. Some data for an attribute can be stored as a time series, such as for values that are regularly reported as part of patient reported outcomes. For example, a date/time 728 can be stored for different instances of the attribute in the time series. The patient data can be logically organized in the data storage in part by condition, and attributes stored for patients can be organized in a nested structured in part by condition.

For storing outcome measures, for each category in which a patient is classified, outcome scores over time are stored. Thus, outcome data 730-1 to 730-N includes a category identifier 732, a time 734 and factor scores 736-740 for each factor for which a score is computed. The example shown in FIG. 7 shows five such factor scores. The outcome value 746, computed as a weighted combination of the factor scores, also can be stored. Examples of other data that can be stored is an indication of the method used to compute the outcome score from the factor scores.

It should be understood that the foregoing description of data representations is illustrative. In some implementations, there may be multiple data storage systems that store data in different formats for different purposes. For example, one database, herein called a standard database, can store such data in a format that is optimized for updating. Another database, herein called the analysis database, can store such data in a format that is optimized for performing queries and analytics on the data, such as a structured data file which stores data in columns in the file and is stored in a distributed file system. Another database, herein called a transaction database, can be used for managing data transactions in real time that input data. Periodically data can be transferred from the transaction database to update the standard database, and the updated standard database can be processed to update the analysis database.

The standard database also can be associated with a variety of data processing modules that extract, transform and load data from various sources, such as various electronic health and medical record systems from a variety of sources, into the standard database. Such processing can include linking data for a patient from different sources, deduplicating data records and normalizing data records across sources. In some implementations, separate databases, or separate access controls on data, can be provided to segregate data that is de-identified from data that identifies patients, providers and/or other entities.

Multiple instances of time data can be associated with a data field. Time can be stored for when an event occurred, when data was received, and when data was generated (such as a report or a value generated by the system to populate and incomplete data field).

Figure 2:
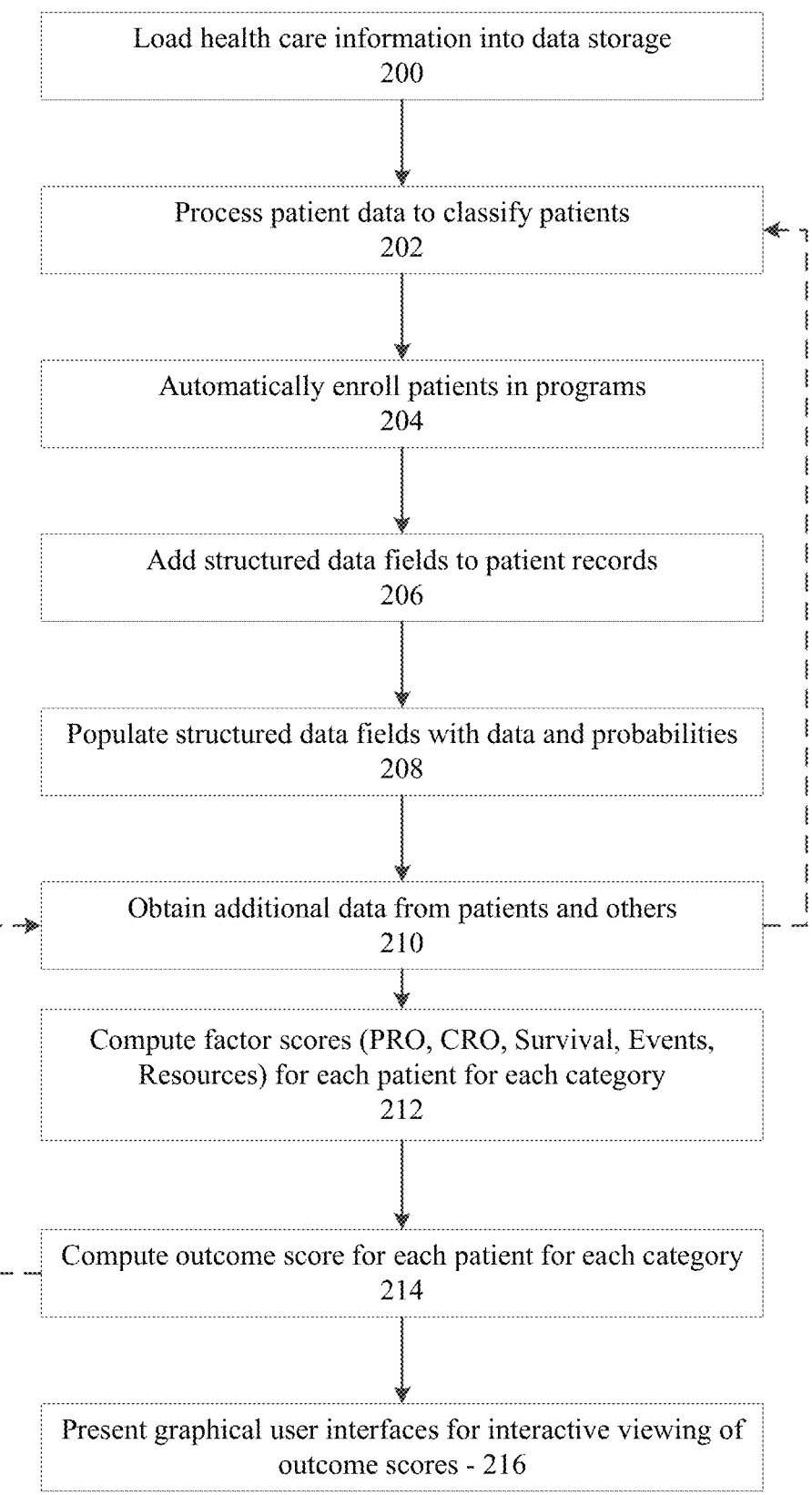
FIG. 2 is a flow chart describing an example implementation of operation of the computer system of FIG. 1.

Turning now to FIG. 2, a flowchart describing operation of a computer system such as shown in FIG. 1 will now be described. While this flowchart and corresponding description presents this operation as a single sequence of steps, these steps can be performed at different points in time, and in a different order. For example, information about patients can be loaded into the system and/or updated at any time. Processing of patient data to categorize patients add and update data fields, and update scores can be performed as daily batch jobs on the databases. Interaction by end users with the database can occur at any time.

Health care information for multiple patients, such as described above, is loaded 200 into the data storage. The patient data is processed 202 to classify patients into categories. A category generally is related to a specific medical condition. In particular, for each available category, a confidence metric, such as a probability, ranking, or other value, is computed and stored for each patient. Where probability is used herein as a form of confidence metric, it should be understood that other forms of confidence metrics also could be used in place of a probability. When such processing is done periodically, the confidence metric of an association of a patient to a category can be viewed over time. Patients then optionally can be automatically enrolled 204 in any health program associated with the category in which the patient is classified.

Any additional data fields related to the category in which a patient is classified are added 206 to the patient record. An additional data field can be a structured data field or an unstructured data field. These additional data fields are populated 208, in part by automatically processing existing patient data. Such automatic processing can result in a confidence metric that the underlying data supports having a particular value stored in one of the added data fields, and this confidence metric also can be stored.

Over time, additional data can be obtained 210, from patients, caregivers and other sources. The computer system can continue to update the patient data, for example by updating existing data fields, adding further data fields, and updating additional data fields and related confidence metrics. Such additional data can be based on, for example, data entry forms for patient reported outcomes, clinical response measures, events of interest, survival and resource utilization. As noted by the dashed line from 210 to 202, the health care information system periodically processes the current patient data as updated over time through steps 202-210.

Periodically, a set of factor scores is computed 212 for each patient, for each category in which the patient is classified. Such factor scores can include values for a patient reported measurement, a clinical response measurement, and one or more of an events of interest measurement, a survival measurement and a resource utilization measurement. The factor scores can be computed using functions defined for the category in which the patient is classified. An outcome score is computed 214 for each patient for each category in which the patient is classified, using an outcome function defined for that category. The outcome function for a category can be any function, such as a weighted function, of one or more factor scores computed for that category. The outcome function for a category is standardized across all patients classified in that category.

Given computed factor scores and outcome scores, various graphical user interfaces can be presented 216 to a user to allow interactive viewing of such information, such as outcome scores and risk factors, for one or more patients.

More details of example implementations of the steps in FIG. 2 will now be described in connection with FIGS. 3 through 5.

Figure 3:
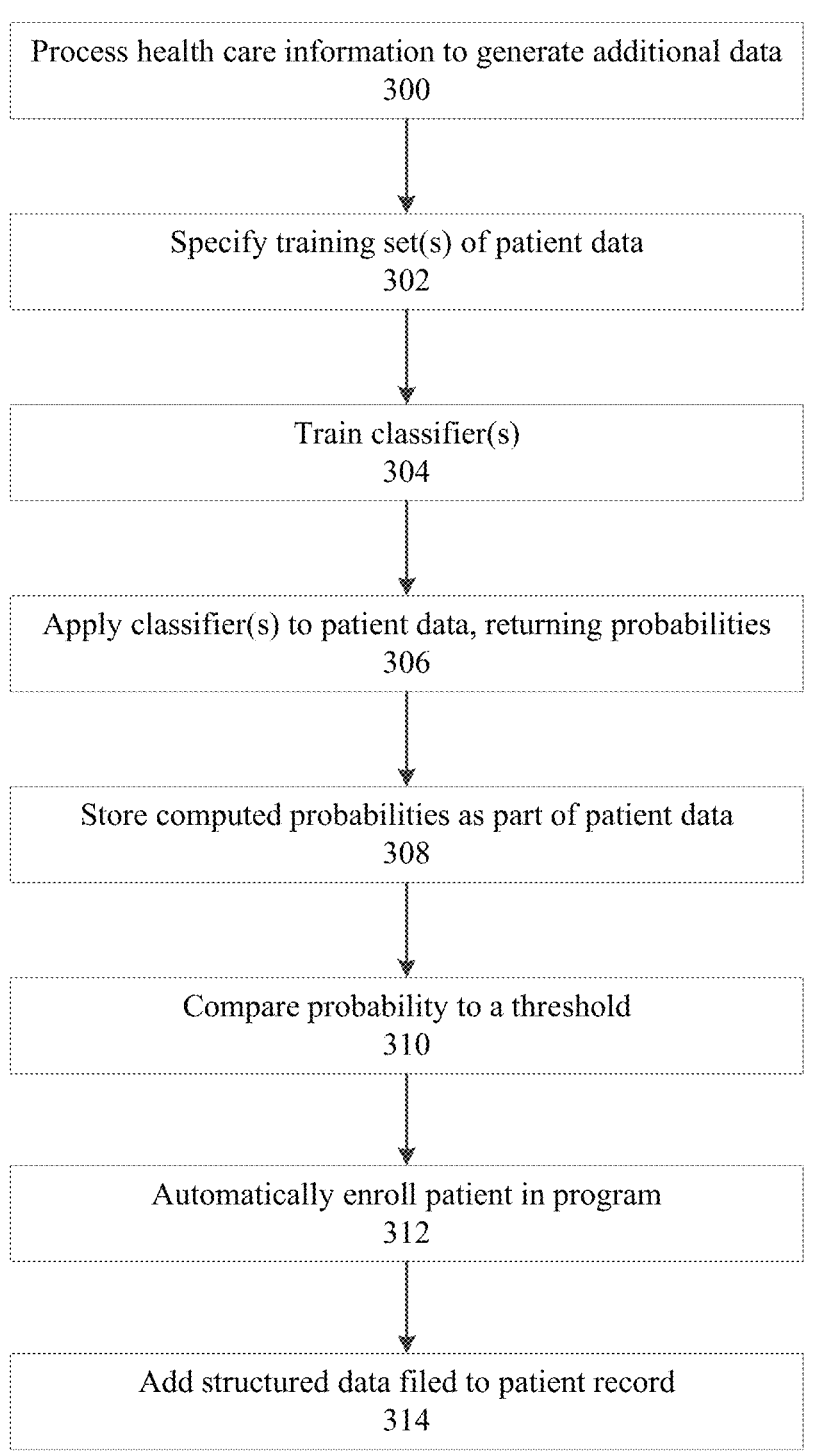
FIG. 3 is a flow chart describing an example implementation of classification of a patient in a category.
Figure 4:
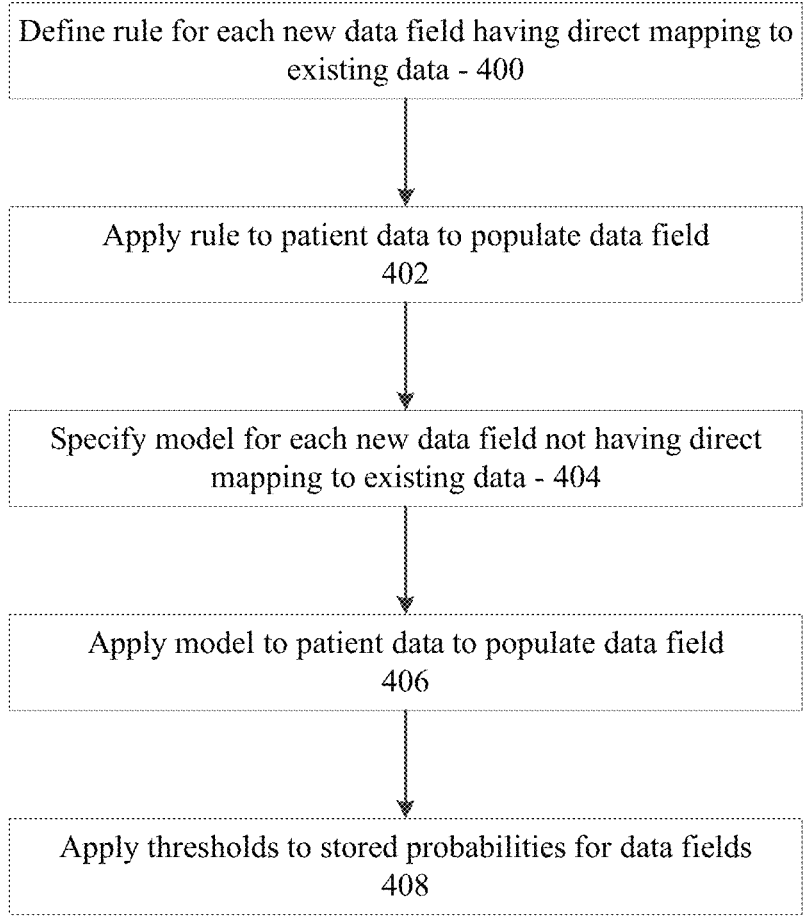
FIG. 4 is a flow chart describing an example implementation of populating data fields with missing values.

Turning now to FIG. 3, a flowchart describing one example implementation for classifying patients into categories.

The health care information in the data storage can be processed 300 to generate additional data, which also can be stored in the data storage. For example, natural language processing can be applied to textual, unstructured data to generate such additional features which in turn are stored in the patient data. For example, natural language processing can extract key words and data types, and apply patterns, defined based on the targeted features, to such key words and data types to detect values for the features. As another example, "deep learning" algorithms can be applied to the patient data to identify features and values for those features. All of the fields of data available for a patient can be considered features from the perspective of training a classifier and classifying patients with a trained classifier.

A training set of patient data is specified 302 for each category for which a classifier is to be built. The training set includes data for patients that are identified as representative of a particular category, i.e., true positives, and can also use data for patients that are identified as non-representative, i.e., true negatives. The category can be defined, for example, as patients that meet criteria for participation in a health program, such as a health outcomes measurement program, or other clinical program or clinical trial or clinical study. The training set can be manually selected by experts, for example. The training set can be automatically selected given criteria that can be applied through queries of the health care information, such as all patients having a particular diagnosis code in their medical records. Given a set of training data for a category, a classifier is trained 304 using conventional machine learning techniques.

The health care information system also can provide information about risks associated with a patient. For example, for each category, known risks can have an associated data field for which the value, a probability, is determined using an associated classifier. The classifier uses a predictive model to determine a probability or risk that a patient will experience a particular condition or event given that patient's current data. Data about such risks also can be presented as part of the graphical user interface. Such risks also may be directly related to, i.e., a function of, some patient data or a factor score or outcome score for the patient. Training of classifiers to determine risks for patients can be generated in a similar manner using a training set of patient data from the database 102, or another database, or by accessing a trained classifier, and then applying the trained classifier to patients data from the database 102.

After one or more classifiers are trained, the trained classifiers are applied 306 to the health care information stored for patients. For each patient, each classifier returns a probability that the patient meets criteria for a particular category. A classifier also can return other values and probabilities associated with those values, such as a likelihood of improving with a particular treatment and a likelihood of experiencing a future event or outcome. If such values exceed a threshold, a notification can be generated and transmitted to a health care provider, or a patient or other individual. The probabilities computed by each classifier for a patient are stored 308 for the patient.

The probability computed for a category can be compared 310 to a threshold for the category to determine whether the patient is associated with that category. The threshold may correspond to qualifying to participate in a health program. If the probability exceeds the threshold for a health program, then the patient can be automatically enrolled 312 in the corresponding health program, which can include adding the patient to a list of enrolled patients for the health program, sending the patient information through a form of electronic communication, such as electronic mail or text messaging. Provisions can be made for a patient to opt out of a health program.

After a patient is associated with a category, additional data fields associated with that category can be added 314 to the patient record for that patient. Such additional data fields can include, for example, targeted data structures based on a case report form for a clinical trial and or registry. Such targeted data structures can be programmed into the system to correspond to, for example, a case report or other set of data that is useful to collect from patients classified in a category. These additional data fields for a category are designed to capture information useful in computing outcomes scores for patients classified in that category.

Given the additional data fields, a process for populating such data fields, and other data fields missing values, with values will now be described in connection with FIG. 4.

A rule can be defined 400 for each new data field for which data in the existing health care information has a direct correspondence. Thus, a rule generally provides a value for a new data field as a function of other existing data fields in a patient's record. Such rules can be predefined for each additional data field to be added for a category. Such a rule also can be defined generically for all patients to provide a value for a data field that otherwise is missing a value. Such rules are executed 402 for each patient that is added to a category to populate the additional data fields for the patient based on the existing data, or for all newly added patients, or for newly added rules.

For some of the additional data fields that are added to a patient record of a patient who has been assigned to a category, there is no direct correspondence with the existing data, or some of the existing data may be incomplete or inaccurate. For such a data field, a model can be specified 404 that predicts a likelihood that the data field is supported by the data in the existing health care information. That likelihood may be represented by a probability, a derived statistic, a rank order or some other means to show the relative likelihood that the data field can be completed using the existing health care information in the system. The model is then applied 406 to the data to generate a likelihood value to be stored for that data field.

Such models can be developed by training a classifier for the data field. In one implementation, experts review a sample of medical records and other data sources and complete the targeted data structures using expert knowledge. In other implementations, rules may be created which look for data in the source data fields to create the sample data set. This sample comprises the training set. This selection of a training set is repeated for each data field which can be completed, such as each of multiple targeted data structures constituting a case report form for a health program. Second, the training data is used to train a series of models to use available data from each medical record to generate values for the data fields with missing values. Such models can generate a probability that the underlying data for a patient record supports a particular value in the data field being populated. Such data fields can represent such information as "Is the patient a current smoker", with a value of Yes or No and a probability, or "What is the level of renal failure", with possible values of Mild, moderate, Severe, and a probability. Such data processing also can be applied to complete the base fields of a patient record that are incomplete. Such data processing also can be applied to identify risk factors for a patient.

A threshold probability can be set for, and applied 408 to, any data field for which a model is used to compute a value and a corresponding probability. When the threshold probability is surpassed by a computed probability related to a computed value for that data field, the value of that data field can be set to the computed value. In one implementation, if the threshold probability is not exceeded by the computed probability from the model, the value for the data field is not set. In other implementations, the value of the data field can be set to a computed value having a highest computed probability. In some implementations, for some data fields, the computed value and the computed probability are the same value which can be stored as the value for the data field. For example, if the stored probability is 0.95, then a calculation using this data field can conditionally use a value based on the stored probability. In such an implementation, the probability can be stored in place of the value for the data field; thus a separate value for the data field can be omitted from the stored data.

Figure 5:
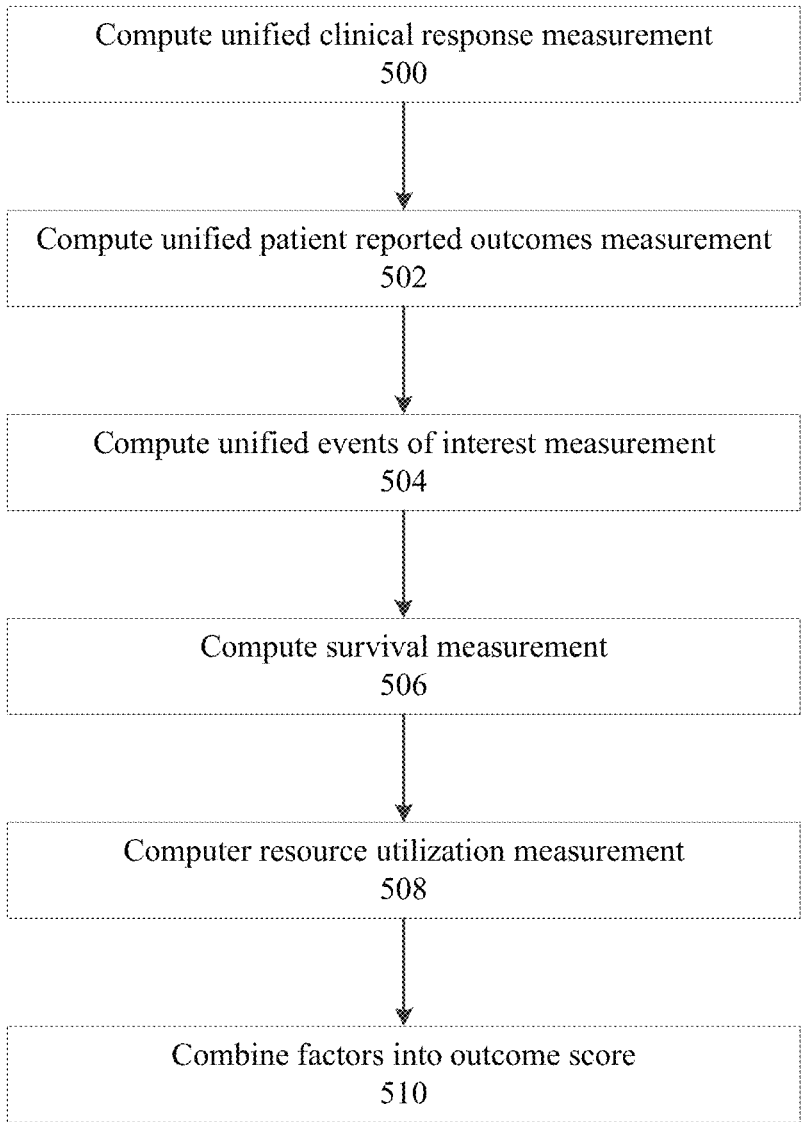
FIG. 5 is a flow chart describing an example implementation of computing outcome scores.

Turning now to FIG. 5, an example implementation of an outcome calculator 160 in FIG. 1, describing how outcome scores can be computed for each patient, for each category in which the patient is classified, will now be described in more detail.

The outcome score so computed uses one or more factor scores that: 1) are specific to a condition; 2) are specific to a time point relative to an episode of care or treatment or at a fixed time interval from baseline or a regular repeated measurement points such as annually; 3) utilize a standardized reporting framework; and 4) create a unified condition specific health score. The unified condition specific health score, also called the outcome score herein, is calculated from at least one of five factor scores based on an algorithm that separately weights each underlying factor score, and combines the weighted factor scores into a single value. The algorithm can vary, for example, by condition, by time point and by user group or by other categorization of the data. By determining a unified condition specific health score at each time point, patient outcome scores can be directly compared from one time point to another, allowing a more standard metric for reporting of outcome scores for each condition.

This standardized framework for generating an outcome score for a condition can be used for each health condition where a patient's factor scores can be computed for a particular point of time, and can use, in this example, up to five factor scores that are related to healthcare outcomes. Those factor scores are patient reported outcomes, clinical response, survival, events of interest and resource utilization.

Survival signifies a patient surviving or not surviving up to that time point. The survival factor is further based on whether death occurs as a result of the condition being reported or not.

Clinical response signifies metrics defined by clinicians regarding how they perceive the patient is doing. These differ by condition. For example, with cancer, clinical response metrics can include progression of disease (growth of tumor, spread of tumor) or regression of disease (reduction in tumor) or control (no progression or regression). Such metrics can be represented as numbers of episodes or exacerbations (e.g. frequency of headaches in a headache patient or number of exacerbations in an asthmatic patient). Such metrics can be represented by a clinical laboratory value or other clinical assessment value or values, e.g., a hemoglobin a1c level in a diabetic, or a viral load in an AIDS patient, or liver function in a cirrhosis patient, or glomerular filtration rate in a kidney disease patient, or clinical rating scale in a rheumatology patient.

Events of interest refers to specifically defined events or encounters that can be predefined by clinicians as demonstrating some unexpected but negative event. Examples of events of interest include, but are not limited to, a surgical complication, such as severing a nerve; an adverse event to a medication, such as an allergic reaction; a readmission to a hospital or visit to an emergency room; a wound infection after surgery; a pneumonia after a general anesthetic; a stroke immediately following a trans-vessel procedure such as a percutaneous angioplasty; or a second heart attack after a first heart attack. Events of interest may be represented as a history of events, and a pattern of events within this history can be relevant to a score.

Patient-reported outcomes are outcomes that are relevant to a patient or caregiver, such as health related quality of life or the ability to perform activities of daily living. There are numerous quality of life measures across many different healthcare conditions. These measures often have different scoring methods and scales going from high to low or low to high. Examples include Likert scale based validated questionnaires and 1-10 or 1-100 mm scales such as visual analogue scales.

Measures that reflect the consumption of resources can include resources noted specifically in cost or as itemized consumption of supplies or personnel hours, or more generally as hospitalizations, treatments, emergency room visits, home care visits, pharmaceuticals and so forth. They can also include non-healthcare costs such as loss of time from work, reduced productivity at work and so forth.

For each condition, at each time point, one or more of these condition-specific factors scores are computed, and then weighted and combined to compute an outcome score. As shown in FIG. 5, the outcome calculator computes one or more of a unified clinical response measurement (500), a unified patient reported outcome measurement (502), and/or a unified events of interest measurement (504) as factor scores. Patient survival may also be reported (to computer a survival measurement 506) at each time point when the information is available. However, if a patient has not survived to the specific time point, then the unified clinical response measurement and the unified patient reported outcome measurement are not measurable for that time point. Resource utilization may also be computed (508) for any interval up through the time point being reported. The outcome calculator then combines (510) one or more of these factor scores to produce the overall outcome score for that patient for that condition.

The computation of outcome scores at multiple time points enables both current status of the outcome score and change in the outcome score over time to be easily reported in simple graphics. This standardized computation of outcome score for multiple patients further enables different user groups to provide different weights to the factor scores that are included in the measurement at any specified point in time relative to a baseline. It also may allow different weights to be provided by panels for the measurements comprising the factor scores as well. For example, a particular group may seek a patient panel to provide input on how to weight the five factor scores for evaluating condition specific outcomes for the one year point. Such a group might also provide input on whether to weight a visual analogue scale or a VR-12 scale in the patient reported summary score differently or equally. The value of this flexibility is that different end users may find that different weightings provide more information to their particular stakeholder group or for particular decision making.

An outcome score based on one or more of the patient reported outcome measurement, clinical response measurement and events of interest measurement can be reported on a numeric scale, such as numeric values or percentages, such as a scale of 0 to 1000, 0 to 100, 0 to 10, 0 to 1, or an arbitrary scale. The unified condition specific health score that may be further modified by a survival score. The unified condition specific health score that may be further modified by a resource utilization score.

The outcome score can be a weighted combination of one or more of these factors. The relative weights can be changed for specific conditions and for specific timepoints of the unified clinical response measurement, the unified patient reported outcome measurement, the unified events of interest measurement, the survival score and the resource score.

In one example, the unified condition specific clinical response measurement can be computed (500) by converting n condition-specific clinical response measurements to n scales normalized on a similar scale for combining otherwise disparate measurements [Constant 1×clinical status measurement A (normalized to common scale)+Constant 2×clinical response measurement B (normalized to a common scale)+ . . . +Constant n×clinical response measurement n (normalized to common scale)] divided by (Constant 1+Constant 2+ . . . +Constant N). This measurement can be converted to a scale of 0-100 where 0 is the worst possible score and 100 is the best possible score.

In one example, the unified condition specific patient reported outcome measurement can be computed (502) by converting n condition-specific patient reported outcome measurements to n scales normalized on a similar scale for combining otherwise disparate measurements [Constant 1×patient reported outcome measurement A (normalized to common scale)+Constant 2×patient reported outcome measurement B (normalized to a common scale)+ . . . +Constant n×patient reported outcome measurement n (normalized to common scale)] divided by (Constant 1+Constant 2+ . . . +Constant N). This measurement can be converted to a scale of 0-100 where 0 is the worst possible score and 100 is the best possible score.

In one example, the unified condition specific events of interest measurement can be computed (504) as an algebraic sum or a weighted sum of each of the specific events of interest. Each of the events of interest can be individually graded for severity using a numerical grading scale with one or more defined clinical criteria. This measurement can be converted to a scale of 0-100 where 0 is the worst possible score and 100 is the best possible score. Such weighting can be determined based on evidence, literature or through data analysis applied to the patient data.

The unified condition specific health measurement can be computed (510) by combining one or more of a unified condition specific patient reported outcome measurement, a unified condition specific clinical response measurement, a unified condition specific events of interest measurement, a unified condition specific survival measurement, a unified condition specific resource utilization measurement.

In one example, the unified condition specific health measurement can be derived using the following algorithm [Constant 1×clinical response measurement A+Constant 2×patient reported outcome measurement B+Constant 3×Events of interest measurement C+Constant 4×survival measurement D+Constant 5×resource measurement E]/(Constant 1+Constant 2+Constant 3+Constant 4+Constant 5) where Constant 1, 2, 3, 4, 5 may be the same or different and may be any whole or fractional number including 0.

In one example, the unified condition specific health measurement can be derived using the following algorithm [Constant 1×clinical response measurement A+Constant 2×patient reported outcome measurement B+Constant 3×Events of interest measurement C+Constant 4×survival measurement D/(Constant 1+Constant 2+Constant 3+Constant 4) where Constant 1, 2, 3, 4, 5 may be the same or different and may be any whole or fractional number including 0.

In one example, the unified condition specific health measurement can be derived using the following algorithm [Constant 1×clinical response measurement A+Constant 2×patient reported outcome measurement B+Constant 3×Events of interest measurement C]/(Constant 1+Constant 2+Constant 3) where Constant 1, 2, 3 may be the same or different and may be any whole or fractional number including 0.

In one example, the unified condition specific health measurement can be derived using the following algorithm [Constant 1×clinical response measurement A+Constant 2×patient reported outcome measurement B]/(Constant 1+Constant 2) where Constant 1, 2 may be the same or different and may be any whole or fractional number including 0.

The various weights in the foregoing computations can be determined by a statistical analysis of a patient data set with known outcomes. The statistical analysis can determine which fields of patient data contribute most to a specific outcome in a category. Weights can be assigned to such fields of patient data to compute factor scores and outcome scores for the category. In particular, a weight can be assigned to each diagnosis code and procedure code. This weight can be applied to compute the factor score using that diagnosis code or procedure code.

As noted above, given ongoing entry of patient reported outcomes from patients and/or caregivers, entry of clinical response measures and entry of events of interest, and periodic classification of patients, automatic enrollment of patients, and computation of outcome scores, such information can be interactively viewed through a graphical user interface. Such a graphical user interface can allow a patient to, among other things, review medical history. The graphical user interface can allow a health care provider to, among other things, review the patient data for one or more patients, compare data, such as outcomes, among patients, and review risks identified for individual patients.

An example graphical user interface for this example implementation will now be described in connection with FIGS. 8-17.

A graphical user interface generally is implemented as part of an application executed on a computer, and can be implemented using interpretable code executed in a browser application. For example the graphical user interface pages can be built as single-page applications (SPA) using HTML5 including CSS and JavaScript. Each single-page application dynamically loads only the necessary resources (pages, styles, code) for the user's current view and action using asynchronous calls to an application programming interface.

FIG. 8 are example graphical user interfaces for use on a client computer for patient entry of patient reported outcomes. At 800 an interface prompts a patient to select a value for a structured data field. In this example, the values are limited to a set of five possible selections. At 804, an interface prompts a patient to enter a value for a structured data field. In this example, the values are on a range represented by a sliding scale. At 802, navigation aids are provided. In response to patient input with respect to such aids, the system can transition between different user interfaces for entering different structured data. In response to patient input with respect to one of the options on a given interface, the system stores the value in the patient's data records. Upon completion of the data entry, the system can recompute and display, at 806, a graphical representation of an outcome score for the condition, updated using the recently entered patient reported outcome data.

Figure 9:
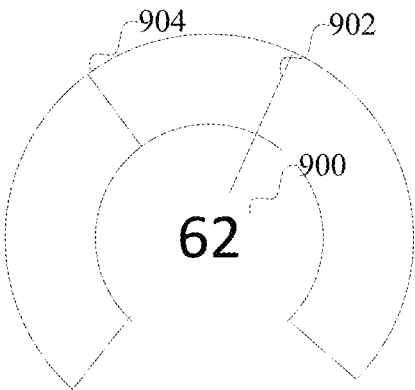
FIG. 9 is an example graphical user interface for use on a client computer to display a graphical representation of a current outcome score to a patient upon completion of data entry for patient reported outcomes.

FIG. 9 is an example graphical user interface for use on a client computer to display a graphical representation of a current outcome score to a patient upon completion of data entry for patient reported outcomes. In this graphical representation, the current score is displayed as a number at 900. The current score also is indicated at a position 902 along an arc representing the range of possible values. A baseline or previous score is indicated at a position 904 along this arc. The appearance of the arc between the positions 902 and 904 can be different from the other sections of the arc, to highlight improvement (such as by making this part of the arc green) or regression (such as by making this part of the arc red).

Figure 10:
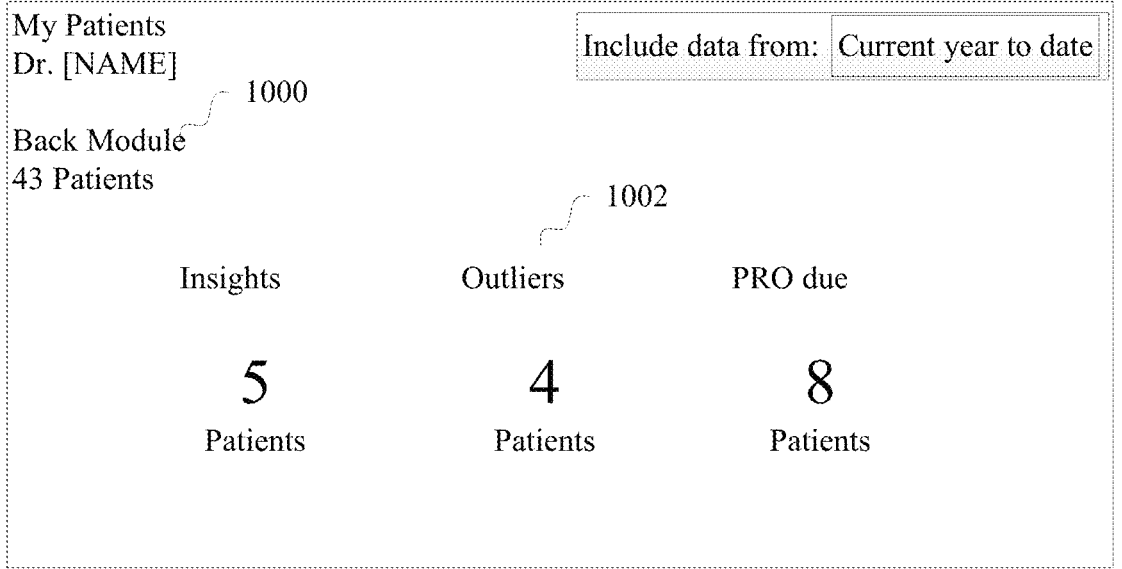
FIG. 10 is an example graphical user interface for use on a client computer to provide a physician's dashboard.

FIG. 10 is an example graphical user interface for use on a client computer to provide a physician's dashboard. This graphical user interface is one example of a navigation-style interface that allows a user to select a subset of patients and then perform analyses and/or view information about patients within that subset. In FIG. 10, the subset of patients is selected by their association with a physician. A variety of different kinds of dashboards can be created for different kinds of users to allow selection of patient subsets and navigation of patients within those subsets.

In FIG. 10, for a given condition, as indicated at 1000, the dashboard can display graphical representation of groups of patients with the condition, such as indicated at 1002. Patients may be grouped by any of a variety of criteria. In this example, patients are grouped by: patients that have "insights" associated with them (such as a classifier, after processing their data, identified a risk of an event occurring); patients that have "outlier" information (such as, after processing their data, some reported data is significantly variant from other patients in the group); and patients that have to input their patient reported outcomes. Such data about the status of these patients can be stored as data fields in the patient data. In response to the physician's input with respect to one of these groups, a more detailed view of the patients in that group can be displayed, such as in FIGS. 11-14. Such groupings can be displayed for each category in which this physician's patients are classified.

Figure 11:
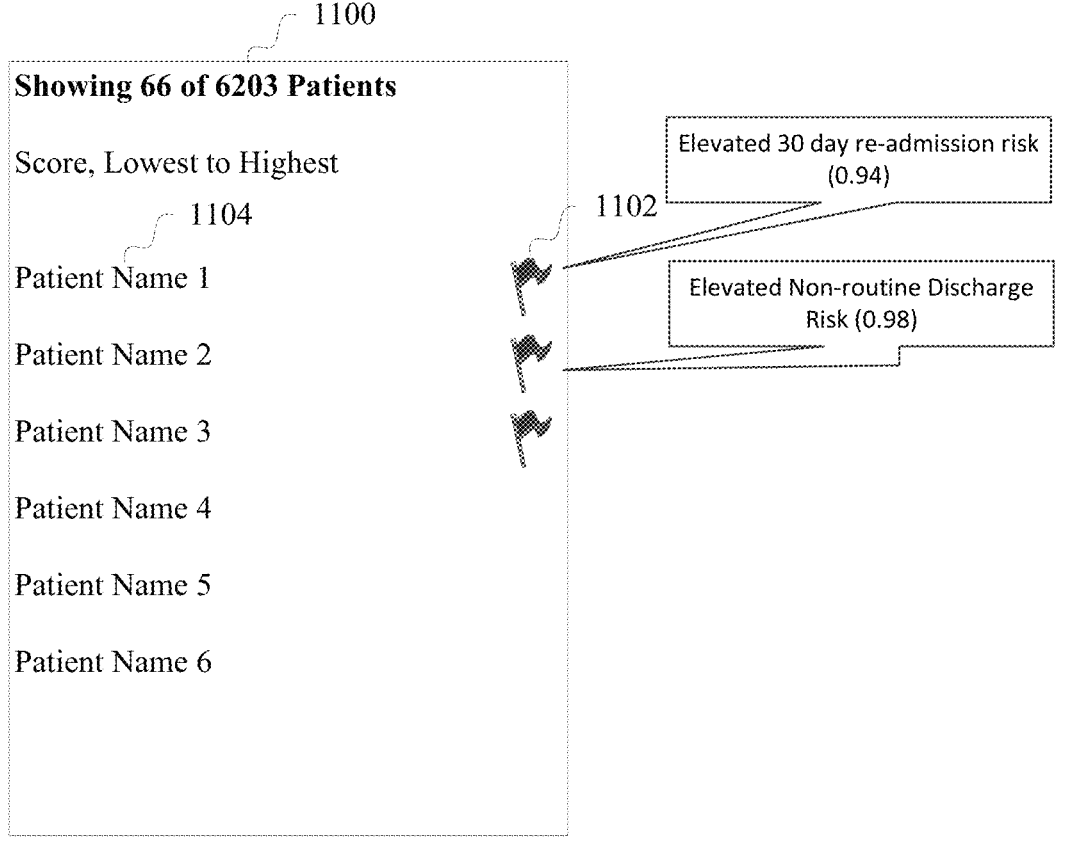
FIG. 11 is an example graphical user interface for use on a client computer to provide a patient list with data indicating patients with detected risks.

FIG. 11 is an example graphical user interface for use on a client computer to provide a patient list with data indicating patients with detected risks. In this example, the system presents a graphical representation of a subset of the physician's patients, such as a list 1100. The subset can be based on, for example, patients in a particular category, i.e., having a particular condition. For each patient having a detected risk flagged in their patient data, an indicator 1102 of that risk can be shown next to an indicator 1104, such as a name, for that patient. The risk indicator can be determined, for example, using a classifier developed for the category of patients which detects patients that may have a risk of an event or condition, using information about patients known to have had that event or condition. The risk indicator for a category may be one of the additional data fields added to a patient record if that patient is classified in that category. Given the displayed list, in response to a physician's input with respect to a displayed representation of a patient, the system can access and display information for that selected patient.

Figure 12:
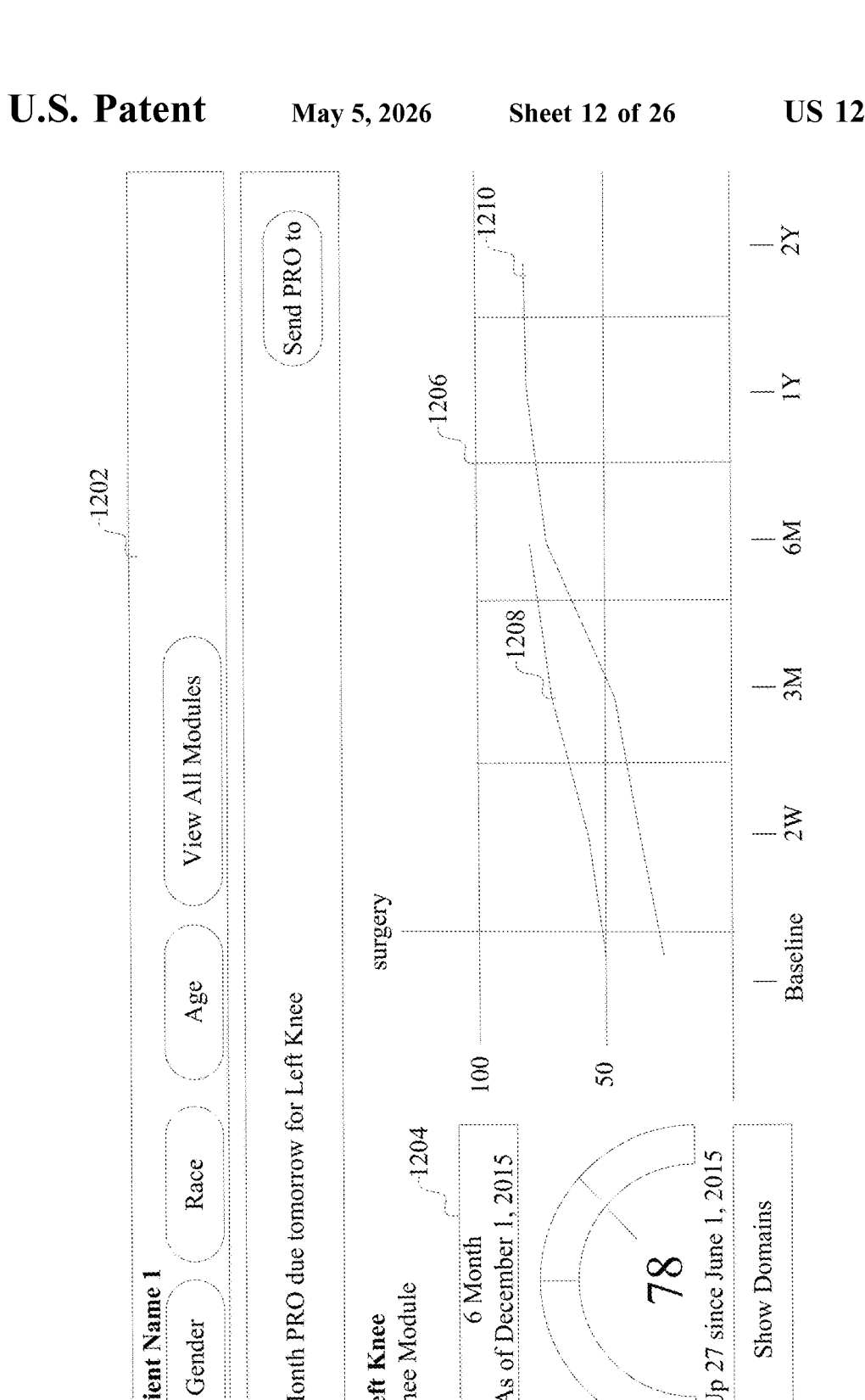
FIG. 12 is an example graphical user interface for use on a client computer for a physician to view data about a patient.

FIG. 12 is an example graphical user interface for use on a client computer for a physician to view data about a selected patient. This interface can include a graphical representation of a patient list 1200. In response to selection of a patient, the information for the selected patient is shown in area 1202 of the display. The displayed information can include a graphical representation of the patient's current outcome score 1204 for the selected condition. This display is similar to the one shown to patients in FIG. 9. A timeline view 1206 of the outcome score over time also can be displayed. The timeline view can show the outcome score of the patient, e.g., at 1208, in comparison to a reference, e.g., at 1210, such as a national average, average of patients of that physician or health care facility, or other reference.

Figure 13:
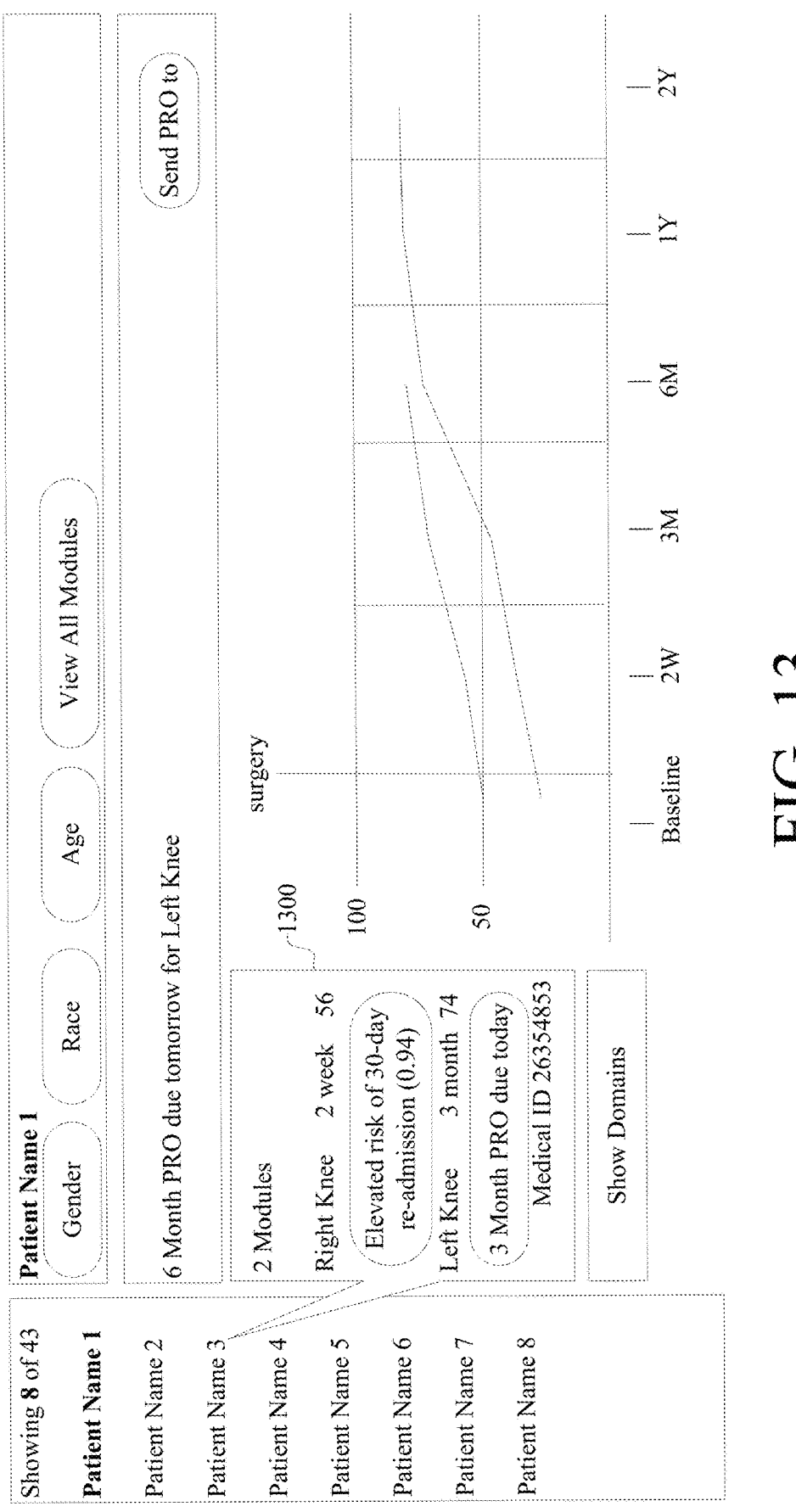
FIG. 13 is an example graphical user interface for use on a client computer showing more detail of use of the interface of FIG. 12.

FIG. 13 is an example graphical user interface for use on a client computer showing more detail of use of the interface of FIG. 12. In FIG. 13 a contextual menu 1300 is shown in response to user input with respect to another patient shown in a patient list. In this example, the patient is identified as having an "elevated risk of 30 day readmission (0.94)". In response to physician input with respect to this contextual menu, the display can switch to a display of data for another patient. Such a menu can include risk indicators similar to those shown in FIG. 11.

Alternatively, the menu in FIG. 11 or 13 or other interface can illustrate "insights" about a risk factor or the outcome score. Such insights are indications of medically modifiable factors that, if modified, would alter the risk factor or outcome score. For one example, instead of, or in addition to, reporting that a patient has an "elevated risk of 30 day readmission", this menu or other user interface element can provide an indication of what patient data results in this elevated risk. For another example, a patient may be identified as having a high risk of infection in surgery. An insight that may be provided in this system is that the patient should focus on managing blood sugar around the time of the surgery. The models described below can provide insight into how changes in blood sugar should affect this risk. More details of an example implementation of how to generate such insights are provided below in connection with the description of FIG. 18.

Figure 14:
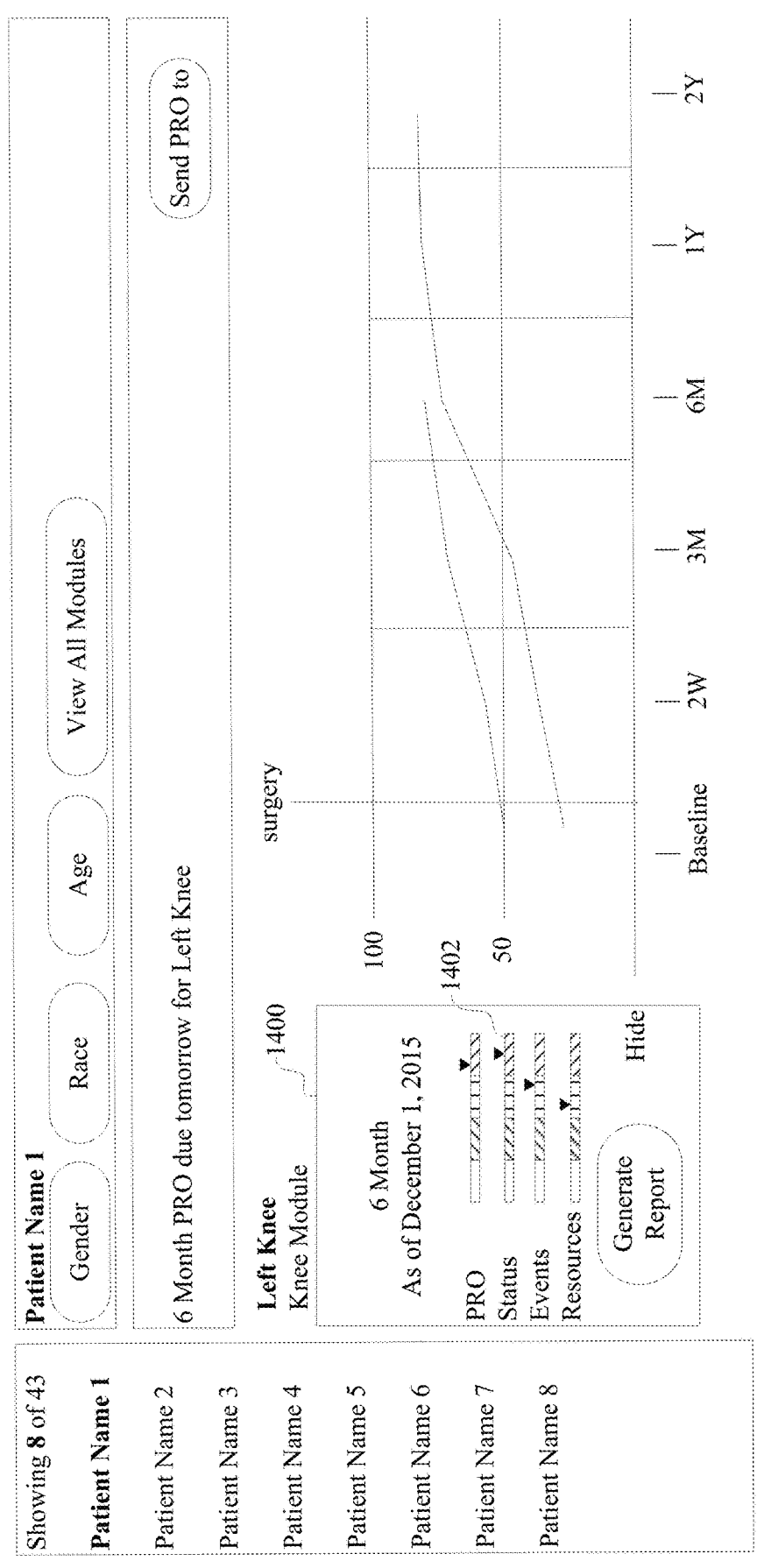
FIG. 14 is an example graphical user interface for use on a client computer showing more detail of use of the interface of FIG. 12.

FIG. 14 is an example graphical user interface for use on a client computer showing more detail of use of the interface of FIG. 12. In response to user input with respect to the displayed outcome score, another graphical representation

1400 of the outcome score is shown. In this representation, a graphical representation of the factor scores, e.g., 1402, are shown. In this example, the factor scores are shown in a range of possible values, with that range shown with different bands of color representing how the factor scores compare to a reference.

Figure 15:
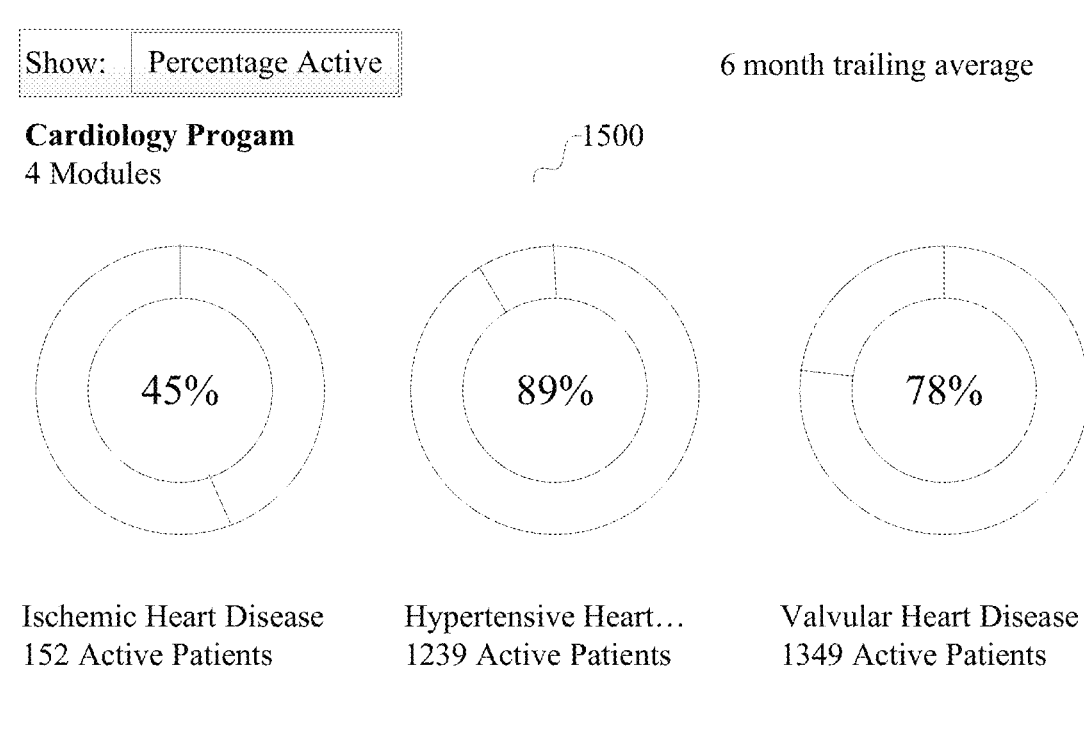
FIG. 15 is an example graphical user interface for use on a client computer to provide an administrator's dashboard.

FIG. 15 is an example graphical user interface for use on a client computer to provide an administrator's dashboard. An administrator can be an individual that is reviewing data for a patient group but who is not the physician or the patient. In general, such an interface will use and present de-identified and/or aggregated data from the patient data. In this example interface, the administrator has a few categories in which patients may be classified, which are shown as a few modules of a cardiology program. Generally speaking, the dashboard includes a graphical representation 1500 of a patient group. For example a 6 month trailing average of outcome scores for all patients in this category can be computed and displayed. A number of active patients in the category also can be displayed. In response to user input with respect to the representation 1500 of a patient group, the system can transition to a display that generates reports. As an example, a comparison report is shown in FIGS. 16 and 17.

Figure 16:
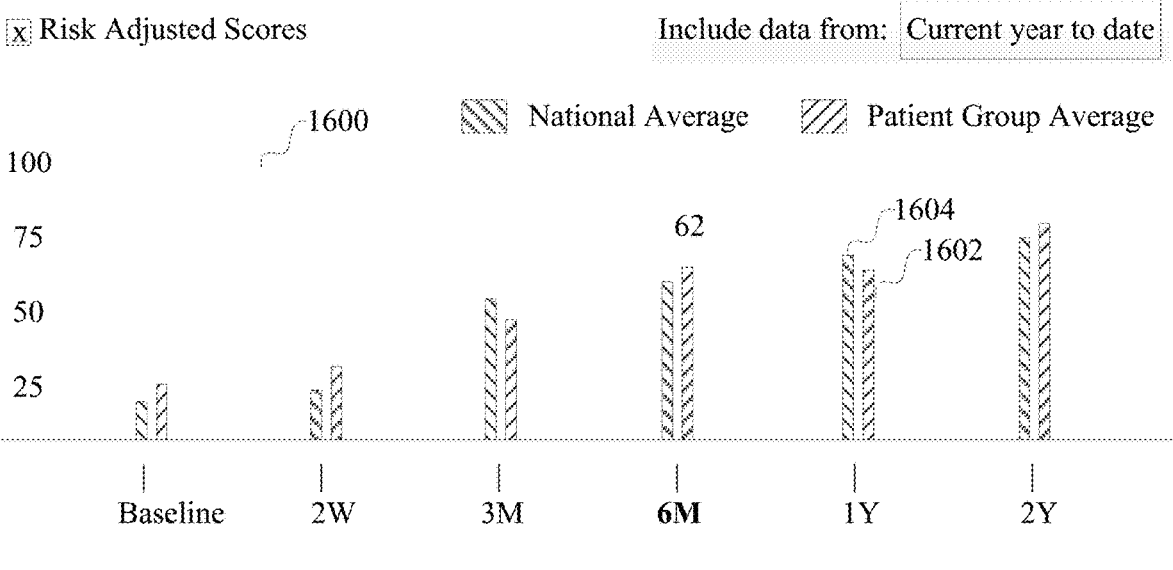
FIG. 16 is an example graphical user interface for use on a client computer to provide a comparison report.

FIG. 16 is an example graphical user interface for use on a client computer to provide a comparison report. This report includes a graphical representation 1600 of a comparison barchart over time. The bars 1602, 1604 represent, respectively, an average patient outcome score (or other score) for a group of patients, and a reference outcome score (or other score), typically for another group of patients, at a given point in time in historical patient data. The reference outcome score can be, for example, a national average, regional average, demographic average or the like. The scores can be risk adjusted and the interface can have a provision for user selection from among different risk adjustment models that apply risk adjustments based on patients' medical data.

Figure 17:
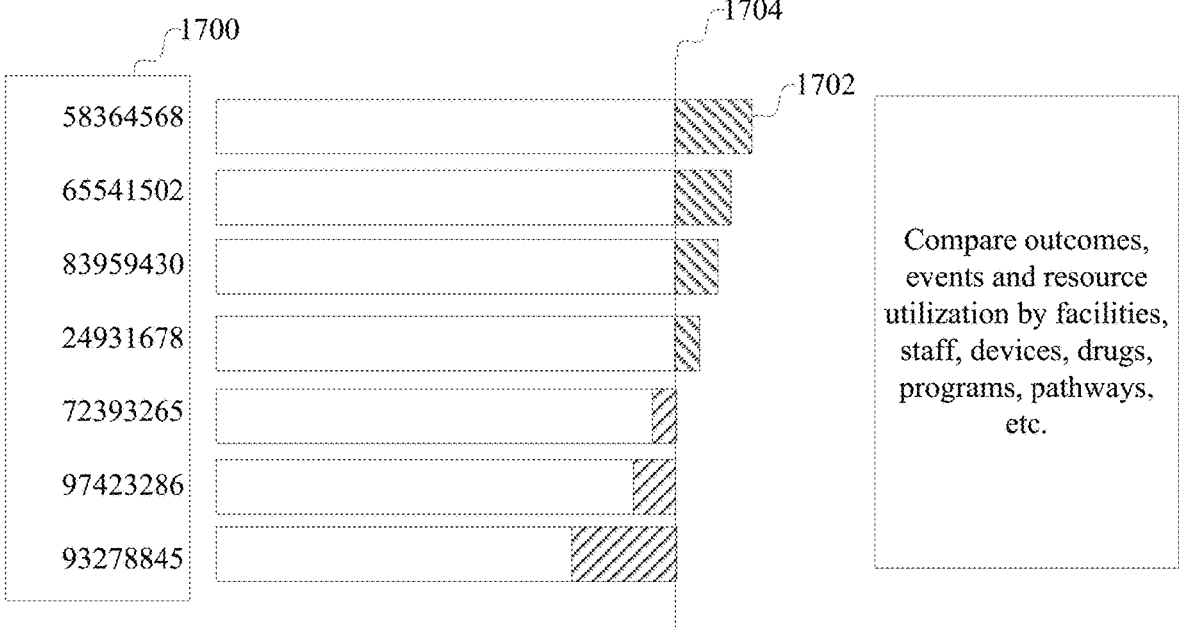
FIG. 17 is an example graphical user interface for use on a client computer to provide another implementation of a comparison report.

Condition scores in FIGS. 16 and 17 can be computed for any group of patients, where the group can be defined using any filtering or searching criteria applied to the patient data. For example, patients can be grouped according to one or more conditions, physicians, treatments, demographic information or any other data in the patient data 102. Within a group of patients, the data as shown in a graph such as FIG. 16, can be further segmented by subgroup at a point in time, and can be further compared using an interface such as shown in FIG. 17.

FIG. 17 is an example graphical user interface for use on a client computer to provide another implementation of a comparison report. Such an interface can be displayed, for example, below the interface of FIG. 16 within the same general display area on the display and interactively changed in response to a selected time point on the interface of FIG. 16. The interface of FIG. 17 illustrates subgroups 1700 of the patient data. For each subgroup, there is a graphical indication of an average score that that subgroup, e.g., 1702 in comparison to a reference 1704, which may represent a national average, group average, other average or an arbitrary reference.

The subgroup of the patient data can be based on any data field or combination of data files in the patient data, such as by facility, health care provider or staff, devices, drugs, programs, pathways, or other patient data field by which a group of patients can be segmented into subgroups for which a comparison of interest can be made. The average score presented in the interface can be any of the factor scores, or the outcome score. For example, one can analyze and compare the resource utilization for patients among subgroups based on the physician. As another example, one can analyze patient reported outcomes for patients among subgroups based on drugs prescribed. A wide range of comparisons of factor scores and outcome scores among different segments of patient populations can be presented.

Figure 18:
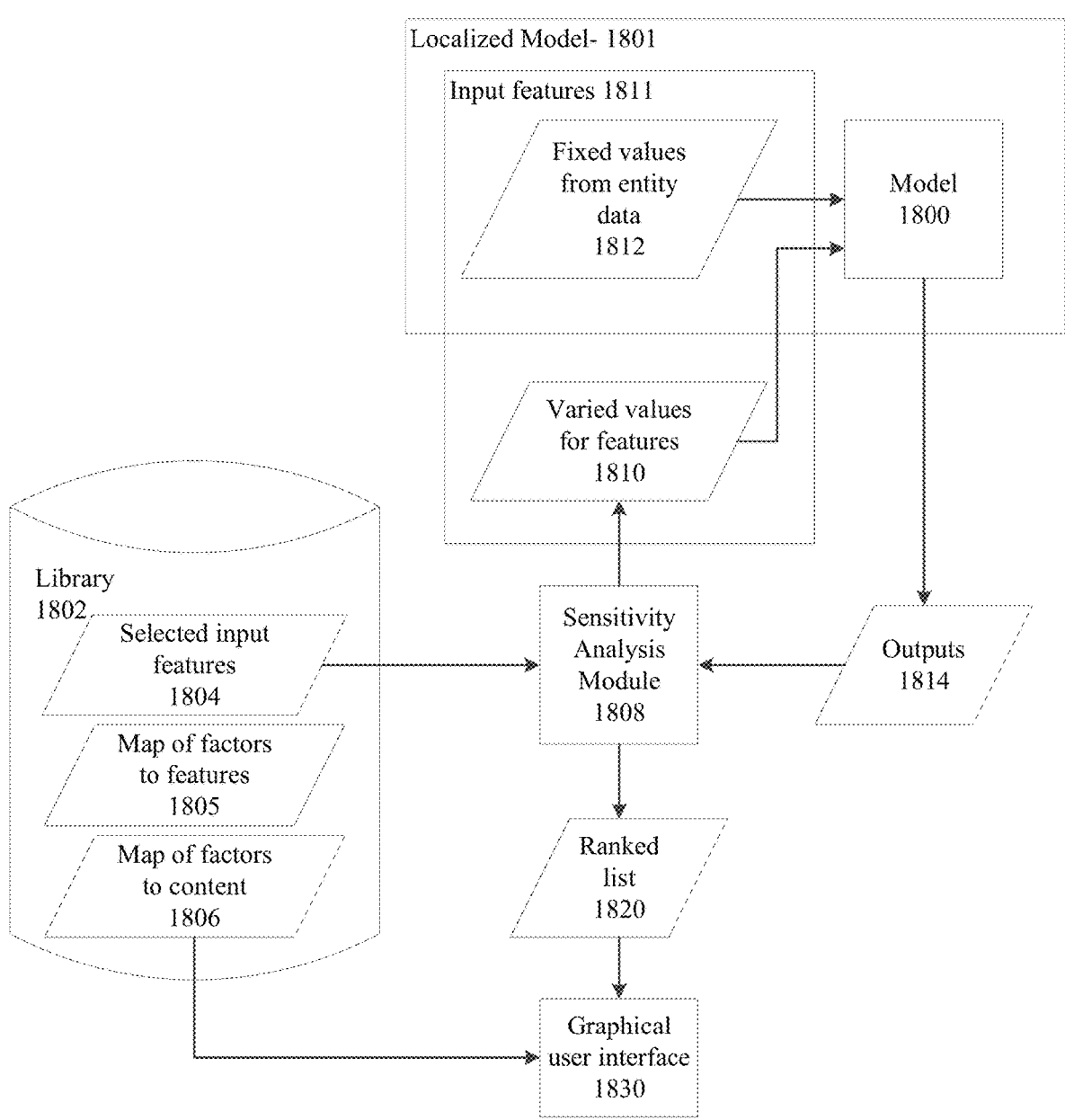
FIG. 18 is a data flow diagram of an example implementation of a locally interpretable, personalized model for explaining the output of a model for a patient.

Turning now to FIG. 18, how the health care information system can generate information that describes how different inputs to a model affect the output of the model, for a given entity, will now be described in more detail. The model can be any model in a health care information system, such as the example system described above. For example, the model can be a model that classifies patients into categories or conditions, or a model that computes risk factors associated with patients, a model that predicts outcomes for patients, a model that computes factor scores or outcome scores for patients, or a model that evaluates provider performance, or a model that predicts costs, or a model that computes a data value for a field with missing data, a model that computes data values for quantities that are estimated based on other data, or a model that estimates a patient health related metric, or a model that estimates a patient medication adherence or health program participation adherence, or a model that estimates a quantity relating to health care provider metric whether predictively in the future or as an estimate of an unmeasured quantity, and yet other models that perform other analyses on health care information. In many cases, the model is trained using supervised machine learning techniques and is a type of machine learning model for which the behavior typically is nonlinear. This technique can be applied to computer models that process other types of data, and is not limited to health care information or the specific types of models described herein.

For example, a risk calculator (e.g., 170 in FIG. 1) may be able to predict with great accuracy whether a patient is at high risk, for example, of readmission to a hospital (such as shown at 1102 in FIG. 11). However, the risk calculator may not provide information about what data for a specific patient resulted in a score indicating high risk, or what can be done to manage or mitigate this risk.

Similarly, any predictive model may be able provide an accurate prediction based on an input, but may not provide information about what data most contributed to such a prediction, or what actions could be taken to change the prediction for that input. Similarly, a classifier may be able to classify precisely an input into a category, but may not provide information about what data most contributed to such a classification, or what actions could be taken to change such a classification for that input. Such techniques, therefore, can be applied to computer models that process other types of data, and is not limited to health care information or the specific types of models described herein.

For the computer system to generate information that describes how different inputs to a model affect the output of the model, the computer system builds a locally interpretable model, or localized model, for a given entity, based on model and on data values for the given entity, and then determines how the output of the localized model for the given entity changes in response to different inputs. The localized model is an approximation of the model which may or may not differ from the model.

As used in this context, the given entity is an entity corresponding to the output of the model. The entity thus can be a patient, a health care provider, insurer, care manager, laboratory, supply provider, vendor, and thus may be an individual, or an organization. Additionally, an entity can be anything for which the model computes a values based on input features derived for the entity. For example, as described above, a model may be used to compute a data value for a field for which data is missing, or a prediction of an outcome for a treatment, or classification of input data into a category. The entity also can be a combination of entities, such as a health care provider and a type of treatment, or a patient and a provider.

Given the localized model, the computer system performs a kind of sensitivity analysis on the localized model for the given entity. Sensitivity analysis, as used herein, refers to applying a different data value for a selected input feature to the localized model, in response to which the localized model for a given entity provides an output, as a way of evaluating what the result of the model would be if the data value for the given entity for the selected input feature were different. In one implementation, the computer system applies one or more different data values to a set of selected input features of the localized model for the given entity, while data values for the remaining input features of the localized model are fixed to data values for the given entity. The localized model can be the model itself. In some implementations, there may be a single different data value for one of the selected input features, in response to which the localized model provides an output indicating what the result of the model would be if the data value for the given entity for the one of the selected input features were different. In some implementations, a sensitivity analysis of the localized model with respect to the selected input features can be performed, for example, by using linear regression, nonlinear regression, or Bayesian sensitivity analysis, or other types of analysis.

The set of selected input features contains those input features of the model for which the local impact on the model for the given entity will be evaluated. The selected input features can be selected from among input features of the model which correspond to explainable factors for the model. An explainable factor is a factor for which variation in values for corresponding input features of the model may have a relevant effect on the output of the model. The computer system described herein assesses the extent of the effect. Such factors may be selected, for example, based on known expected effect on the output of the model, or based on known importance of the factor without prior knowledge of expected effect on the output of the model, or for any other reason. For example, in health care systems, factors that are known to affect risk or that are medically important may be selected as explainable factors. As an example, the set of selected input features can include age for a patient and the impact of the age of a given patient on the output of a model can be determined. An explainable factor can be an input feature or can be data that can be mapped, either directly or indirectly, to an input feature. For example, an explainable factor can be, for example, a blood pressure measurement or age, but the corresponding input feature of the model being analyzed may represent that data in a different format.

The computer system uses the remaining set of input features to the model, i.e., those not in the set of selected input features, to create the localized model for the given entity. In one implementation, the localized model is created by setting the data values for a set of the input features of the model, other than the selected input features, to the data values for those input features for the given entity. In one implementation, the localized model is created by generating another, local model for the given entity, based on the model and on the data values for the given entity.

In one implementation, to create the other, local model, i.e., a localized model derived from an original model, a type of model for the localized model is selected, and a training set for this type of model is created based on the original model and data for the given entity. In particular, for multiple different combinations of different values, taken from a range of values for each of the input features in the set of selected input features, with the remaining input features of the original model fixed to the data values for those input features for the given entity, the output of the original model is obtained for each different combination. These different combinations and their corresponding outputs from the original model define a training set. The localized model is then trained using this training set. After training the localized model, sensitivity analysis can be applied to it inputs, which correspond to the set of selected input features.

The results of the sensitivity analysis performed on a localized model for a given entity indicate which of the selected input features or factors, whether explainable, actionable or medically modifiable, which were not fixed based on the data for the given entity, have the most impact on the output of the model for that entity. The system can present information indicating the effect of one or more of the input features or factors on the model. For example, it can rank input features or factors, in order of impact on the result from the model for the given entity, based on the output of the sensitivity analysis performed on the localized model for that entity. It is possible that different features or factors may be identified as having the most impact for respective different entities.

The set of selected input features can be stored in a data structure in a library for use for multiple entities and multiple models. For each of the selected input features, the library also can store one or more respective different data values to be used in analyzing localized models for entities. The set of selected input features or the explainable factors further can correspond to actions which can be performed with respect to the given entity, such as a particular treatment or behavior change for a patient. This kind of feature or factor is called an actionable factor herein. A set of actionable factors also can be stored in the library, representing actions which can be performed with respect to the given entity, wherein the library can store a mapping between each actionable factor and one or more respective input features in the set of selected input features. The library further can include, for each actionable factor in the set of actionable factors, human-understandable content describing the actions which can be performed with respect to the given entity.

The actionable factors can be medically modifiable factors. A medically modifiable factor is a factor, such as a treatment, intervention or other factor that can be acted upon with respect to a patient, under direction of a health care provider. Typically such a factor can be a treatment, such as a dosage of a medication, and an expected change in patient data due to the treatment, such as a measured laboratory result. The data representing the medically modifiable factors, and a mapping between them to the set of selected input features, can be stored in the library. In the library, these medically modifiable factors also can be mapped to an associated set of suggested direct or indirect actions for the patient. The system can rank medically modifiable factors in order of risk mitigation for a patient based on the output of the sensitivity analysis performed on the localized model for that patient.

Referring to FIG. 18, the model 1800 represents the model to be characterized. For example, one may wish to characterize, as the model 1800, a risk calculator 170 or an outcome calculator 150 or a patient classifier 104 from FIG. 1. Generally speaking, the model 1800 has an input through which the model receives data values for a plurality of input features 1811, and has an output through which the result of the application of the model to the input data values, such as a classification of the input, prediction based on the input, outcome or factor score computation, or risk assessment associated with the input, is provided as the model's output 1814.

The health care information system can includes a library 1802 which stores one or more data structures in computer storage for use in analyzing the model. Using a library 1802 simplifies the process of setting up and analyzing the model 1800 for multiple entities, for explainable or risk driving factors, different treatments or interventions, and other actions, and for storing corresponding content for use in the graphical user interface. The library, for example, includes data 1804 representing the set of selected input features for which a sensitivity analysis of a localized model for a given entity will be performed. For each of the selected input features, the library also can store one or more respective different data values to be used in analyzing localized models for entities.

In the example shown in FIG. 18, the library also has data 1805 that lists explainable, actionable and/or medically modifiable factors, and provides a mapping between these factors and the set of selected input features 1804. There is a mapping between each of the factors, whether explainable, actionable or medically modifiable, and one or more respective input features in the set of selected input features.

Also, the library can store data 1806 that maps the set of selected input features, or the factors, to human-understandable content. Such content may, for example, describe the actions which can be performed for or by the given entity, or provide a user-friendly description of the factors affecting the model output, or otherwise help explain the model output. Such content can be presented to a user, such as a patient or health care provider, suggesting direct or indirect actions for the patient or health care provider to take corresponding to the selected input features. Such content can include, for example, prose descriptions in a natural language, images or other data about the medication, its dosage, its benefits, and other information.

There are a number of ways to generate a library 1802. The data 1805 mapping actionable factors to the selected input features 1804, and the data 1806 mapping content to such factors or features can be constructed, for example, from expert knowledge or analysis based on health care literature. The data 1805 mapping factors to features also can be constructed in part during the training phase for the model 1800. A training set can be analyzed to train a transformer that maps explainable or actionable factors to complex predictive features used by the model 1800. The mapping created by such a transformer can be stored in the library 1802. The mappings 1805 and 1806 can be in the form of a data structure, stored in memory or other computer storage, which associates each factor, on the one hand, which one or more respective features of the model to which the factor is mapped, and, on the other hand, one or more data elements, such as text, images or other data, which can be presented on a computer in human readable form, to which the factor is associated.

In one implementation, given the set of selected input features of the model 1800, and data values for a given entity for the other input features, the computer system instantiates a localized model 1801 for the given entity. Data values for the given entity for a first set of input features, other than the selected input features, are used as fixed input values 1812 to the model 1800. The model 1800 is thus reduced to a localized model 1801 for the given entity for which only a second set of input features, the selected input features 1804, can be varied. This localized model 1801 can be a simplified local (as applied to the given entity) representation, or approximation, of the model 1800, derived using the data values for the given entity and using the model, instead of a localization of the model 1800 based on fixed input values applied to the model itself. This simplified model can be linear or nonlinear, and can be based on any type of model, such as a Bayesian model, expert rules, deep learning algorithm, natural language processing, support vector machines, conditional random fields, random forest, logistic regression, decision tree, maximum entropy, artificial neural networks, genetic algorithms, or other classifier or predictive model, or combination of such models, or other type of model. A model can be built using a training set, in which case the model can be any model for which parameters of a function can be trained by minimizing errors using a set of training examples That analysis of the model 1800 also can be based on varying one of the selected input features 1804 or one of the actionable or explainable factors 1805 at a time.

The sensitivity analysis module performs sensitivity analysis on the localized model, which has been personalized to the given entity, by varying one or more values 1810 for the selected input features 1804 while maintaining the values 1812 for the first set of input features constant. A sensitivity analysis module 1808 determines, from among the set of selected input features 1804, or actionable factors 1805 corresponding to them, which contribute most to the output of the localized model 1801 for the given entity. The sensitivity analysis module 1808 can implement any of a variety of sensitivity analysis techniques, including but not limited to linear regression, nonlinear regression or other nonlinear model, and Bayesian sensitivity analysis, or other computation that has the effect of computing a measure of the sensitivity of the model 1800 output to each factor in the Library 1802.

Generally, the sensitivity analysis module 1808 varies at least one value 1810 from among the selected input features to obtain an output 1814. In some analyses, the values 1810 are varied over suitable ranges for each of the selected input features. The sensitivity analysis module 1808 applies values 1810 to the localized model 1801 which is based on fixed values for the given entity for the other input features 1812. In response, the localized model 1801 provides outputs 1814.

The sensitivity analysis module 1808 analyzes the outputs 1814 obtained in response to different data values 1810 for the selected input features, to produce a ranked list 1820 of the features 1804 or factors 1805. The ranking can be performed by computing scores indicating how much the output 1814 of the localized model 1801 for the given entity changed in response to the different values applied to the input. Such results can be stored with data for the given entity.

A graphical user interface 1830 receives results from the sensitivity analysis module 1808, whether directly or indirectly through data storage and generates graphical elements for presenting information to a user on a display. The graphical user interface 1830 can access data 1806 from the library, which includes content associated with the selected input features used in the sensitivity analysis. The graphical user interface 1830 can present such content, and indications of the ranking of the selected input features, through an output device to an end user of the health care information system.

The information from data 1806 related to the ranked features or factors 1820 can be presented in a graphical user interface such as shown in FIGS. 11 and 13, in addition to or instead of the indication of the risk factor or other output from the model 1800. As a result, using the example of FIG. 11, instead of or in addition to reporting that a patient has a high risk of re-admission, the user interface can convey which medically modifiable factors and how to mitigate those factors, or which explainable factors that provide understanding contribute most to this risk.

The graphical user interface 1830 also can be configured to receive input from the user to experiment with modifying the set of selected explainable variables and/or the medically modifiable factors, and visualizing the results from the model 1800 given such modifications.

The graphical user interface 1830 thus provides, for each entity, a personalized or individualized explanation of the model's output for that entity based on selected variables. The impact of a proposed intervention can be maximized by ranking the actions in order of risk mitigation. Separate lists of interventions can be provided for a doctor and a patient.

The library 1802 allows the sensitivity analysis 1808 and the graphical user interface 1830 to be used for many different types of models. Given a specified model, a given entity, and set of selected input features the sensitivity analysis module 1801 can be applied to a localized model 1800 based on the model and on data values for the given entity for input features of the model other than the set of selected input features. Also, the graphical user interface 1830 can be used for many different implementations of a sensitivity analysis module 1808.

The sensitivity analysis can be performed, i.e., the sensitivity analysis module can be run, at different times for different purposes. For example, when data for a patient is being viewed in the graphical user interface, information about risks for that patient can be displayed. In response to input from a user, the system can generate and can display further information for that patient based on the sensitivity analysis. As another example, when data for a patient is being prepared for viewing in the graphical user interface, sensitivity analysis can be performed and its results can be presented in the graphical user interface. As another example, a group of patients can be selected, and sensitivity analyses can be performed from the selected group of patients to generate and store data that will be used later. For example, such information can be performed on data for a set of patients that a health care provider is about to see the next day, or the next week, or that have been seen over a period of time. The results of the analysis can be stored in the patient data and provided as part of the graphical user interface when data for the patient is accessed and viewed.

An example implementation also can be developed using techniques described in "'Why should I trust you?' Explaining the Predictions of any Classifier", by Marco Ribeiro et al., in *Proceedings of the* 22*nd ACM SIGKDD International Conference on Knowledge Discovery and Data Mining* (KDD 2016), pages 1135-1144.

Figure 19:
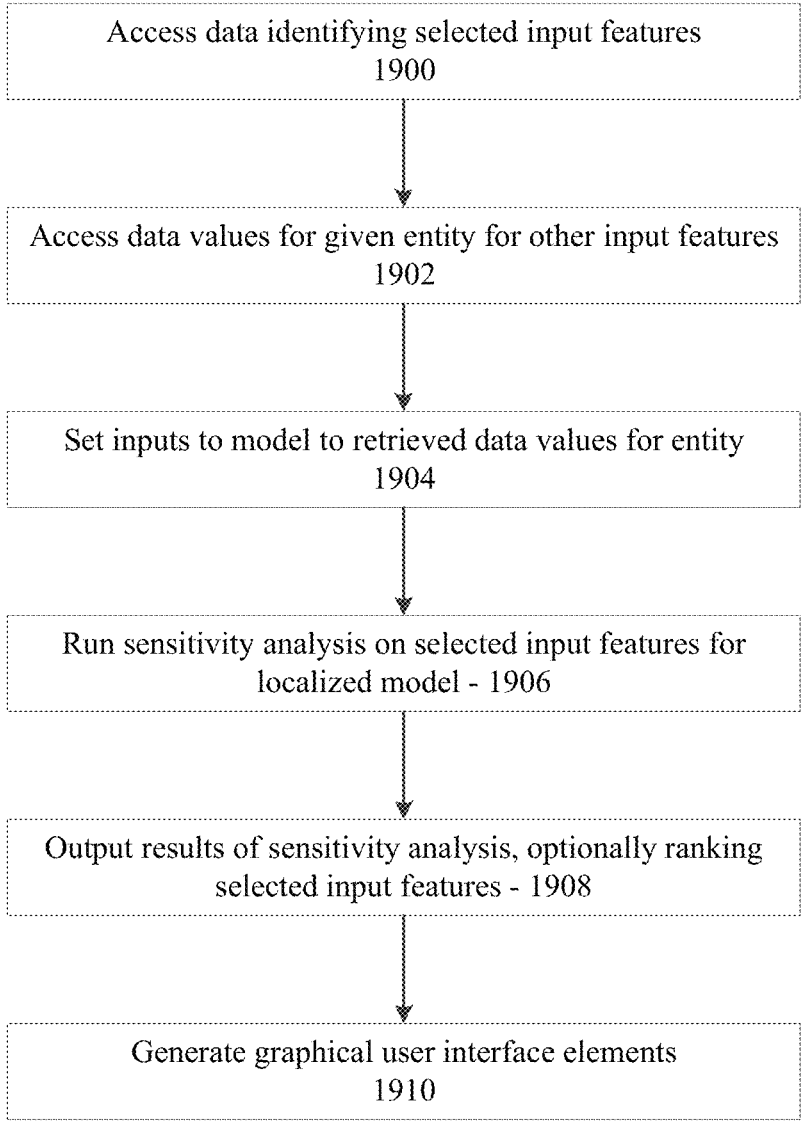
FIG. 19 is a flow chart describing an example implementation of a process performed using the system of FIG. 18.

A flowchart describing operation of the computer system shown in FIG. 18 will now be described in connection with FIG. 19.

Given a model to be analyzed and a given entity, for which the model provides an output, a localized model is created. In particular, the computer system accesses 1900 a data structure storing data identifying a set of selected input features of the model. The computer system accesses 1902 a data structure storing data for the given entity, such as patient data for the given patient, to retrieve data values for the input features of the model other than those in the set of selected input features. The input features for the model are set 1904 to the data values retrieved from the data for the given entity. A sensitivity analysis is then run 1906 on the localized model, by varying one or more data values for the selected input features. The computer system outputs 1908 the results of this sensitivity analysis, optionally ranking the selected features according to their relative impact, for the given entity, on the output of the model. The computer system can generate 1910 graphical user interface elements, such as for graphical user interfaces in FIGS. 11 and 13 and 21.

Turning now to FIG. 20, an illustrative example implementation of data structures stored in the library 1802 will now be described. The example in FIG. 20 illustrates data identifying selected input features 1804, a mapping of factors 1805 to such features 1804 and content associated with features or factors 1805. Such data structures may be stored as data files, such as configuration files, for a computer program, or stored in a database accessed by the computer program, or stored in memory by the computer program during execution.

The selected input features 1804 can be represented by a list 2040 of N selected input features, where N is a positive integer greater than 1. Each feature can have an identifier 2042-*n*, corresponding to how the feature is identified by the model, and optional other data 2044-*n*, such as a text name or different data values to be used in sensitivity analysis, where n is the nth input feature from among the N selected input features.

The mapping 1805 between factors and input features can be represented by a list 2050 of M factors, where M is a positive integer greater than or equal to 1. Each factor can have an identifier 2052-*m*, where m is the mth factor from among the M factors. For each factor, the data structure stores a list 2054-*m* of one or more feature identifiers to which this factor is mapped. The feature identifier corresponds to how the feature is identified by the model. Each factor can have other optional data 2056-*m* associated with it, such as a text name or different data values to be used for the one or more features 2054-*m* for sensitivity analysis. In another implementation, mapping 1805 can be implemented by mapping each input feature 2042-*n* to one or more factors.

The mapping 1806 of content to the factors 1805 or content to the selected input features 1804 can be represented by a table 2060 containing X records 2062, where X is a positive integer greater than or equal to 1. Each record 2062-*x*, where x is the xth record from among the X records, can include an identifier 2064-*x* of a factor or feature, and associated reference to content 2066-*x*. Each record can have other optional data 2068-*x* associated with the content for use by the graphical user interface 1830 in selecting and/or presenting the content.

FIGS. 21A-21F are illustrative examples of a graphical user interface.

In FIG. 21A, the health care information system can provide information about a risk profile for a patient. For example, the system can provide an indication of a first risk score, such as "Future Resource Utilization", and a second risk score, such as "Readmission". In FIG. 21A, the graphical user interface presents two textual elements for the first risk score, namely a name 2100 and the score 2102. Similarly, the graphical user interface element presents two textual elements for the second risk score, namely a name 2104 and the score 2106. The scores 2102 and 2106 could be presented in different way, including graphically, such as a position in a graphical representation of the range of possible values for the score. The graphical user interface can present a comparison, or benchmarking, of statistics of this score within a larger population, e.g. average or median score over all patients in the database of same age and gender as the patient. In the health care information system, the first and second risk scores are computed for each patient using a model. For the given patient for which the scores are shown in the graphical user interface, the input features or explainable factors for that model which most affect the risk score for that patient can be computed using the techniques described above in connection with FIGS. 18-20. These features or factors can be identified, and ranked, and further information can be provided, through the graphical user interface as shown in FIG. 21A.

For example, for the first risk score 2100, the graphical user interface presents a description of the first, second and third explainable factors, 2108, 2110, and 2112, respectively, ranked in order of the most significant impact on the first risk score, for the given patient and the model for computing the first risk score. For example, the first factor 2108 is due to a chronic condition for which mitigating medications may result in a reduced score. The second factor 2110 indicates that the number of procedures the patient had in the past year explains a higher score. Such a factor may be an explainable factor for the model, but is not actionable. The chronic condition of leukemia is the third most impactful factor 2112.

Similarly, for the second risk score 2104, the graphical user interface presents a description of the first, second, third, and fourth factors, 2114, 2116, 2118, and 2120, respectively, ranked in order of the most significant impact on the second risk score, for the given patient and the model for computing the second risk score. For example, the first factor 2114 indicates the number of hospital stays in the prior year had the most impact on the output of the model for this patient. The second factor 2116 indicates that the high future resource utilization score also helps to explain a higher readmission risk score. The third factor 2118 indicates that a mitigating medication could reduce this risk score. Finally, age is also a significant contributing factor 2120.

Turning to FIGS. 21B-21F, a sequences of displays for the graphical user interface illustrate a sequence of processing that the user can direct the health care information system to perform to assess effects of inputs on the model and evaluate actions. In the FIGS. 21B and 21C, the interface presents a graphical element 2130 which indicates a probability, in this case likelihood of improvement in quality of life after knee surgery. A sequence of further illustrations indicate current patient reported values for these components 2132, 2134, and 2136 of this outcome, and corresponding probability levels 2138, 2140, and 2142, in this case indicating components of quality of life and related probabilities that the patients experience of these components will improve. Yet further components can be presented. In this example, those components are difficulty with daily life functions, difficulty with recreational activities, and knee pain and stiffness.

The probability indicated 2130, and values reported for components such as 2132, 2134, and 2136 and other components, can be determined by a model that can be characterized by the techniques described herein.

Figure 21C:
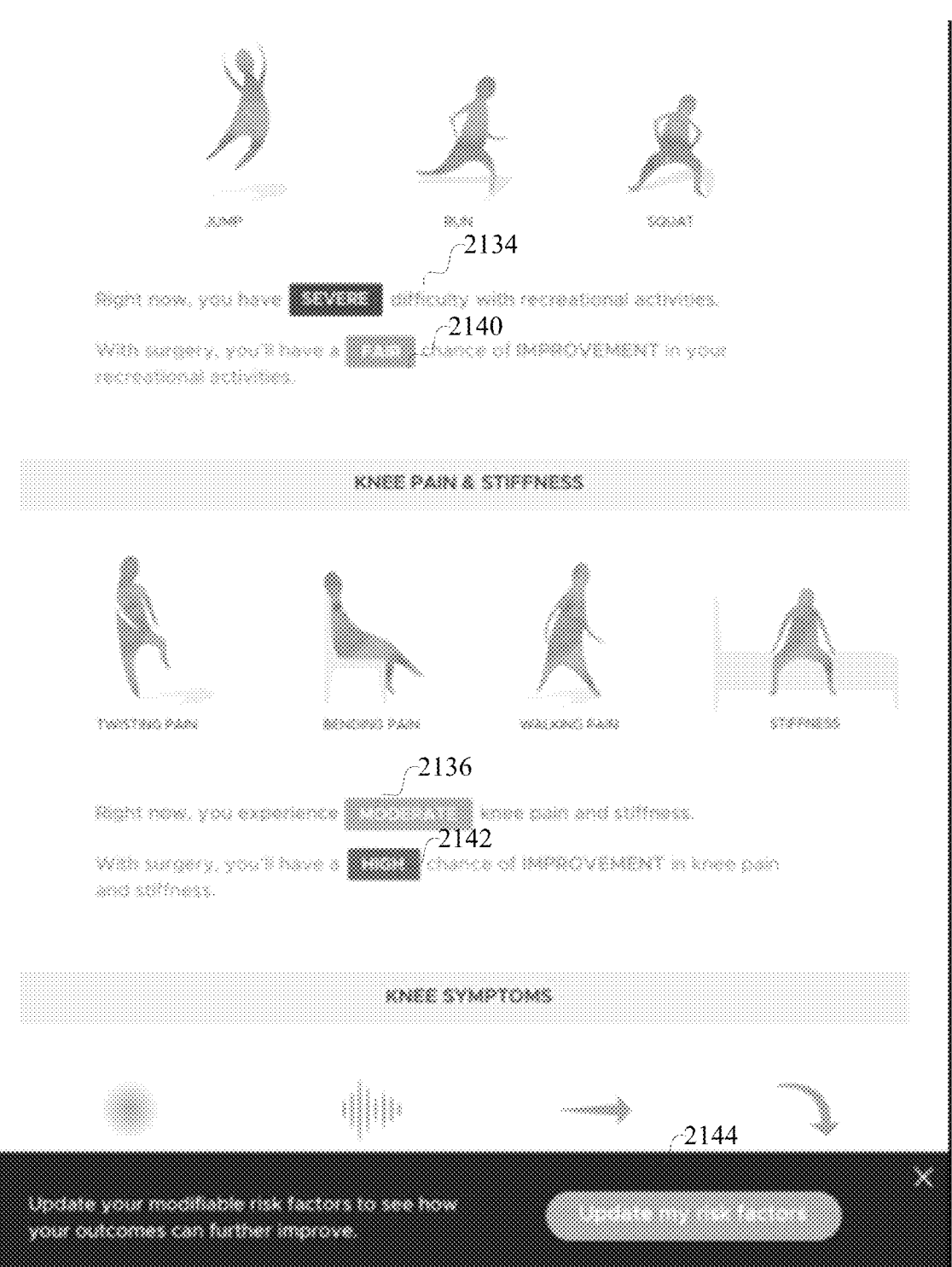
Figure 21D:
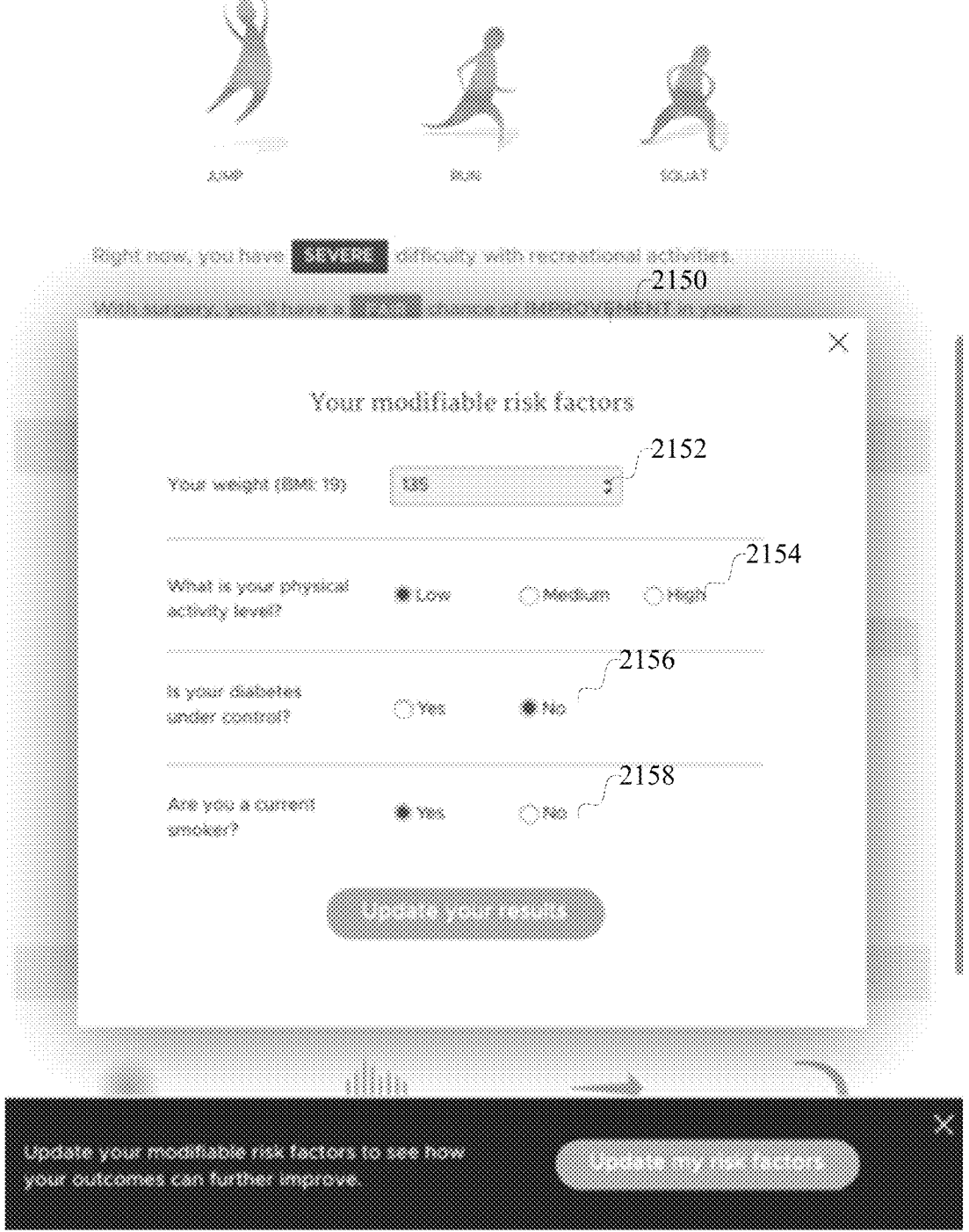
Figure 21E:
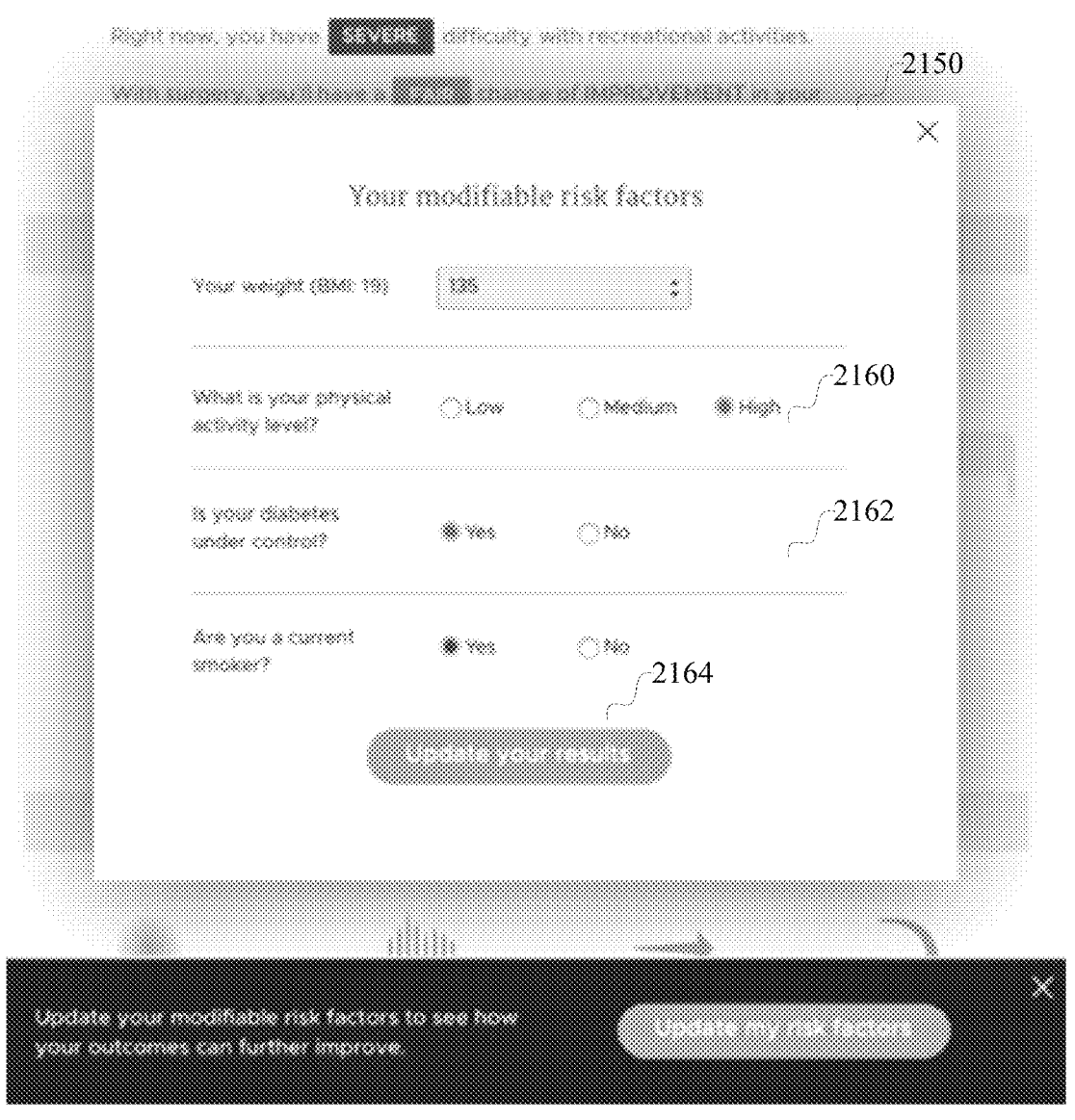
Figure 21F:
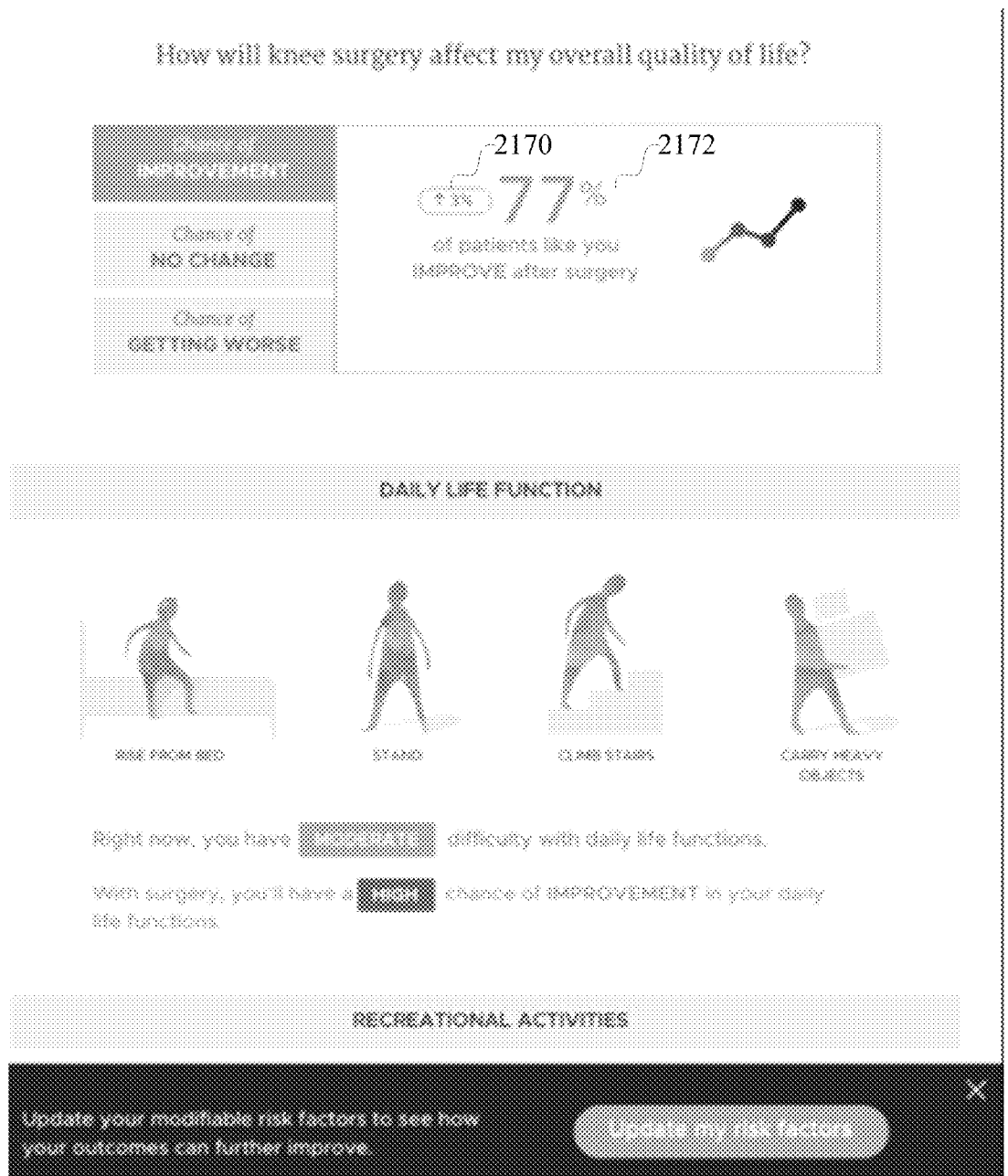

In the example shown in FIGS. 21B-21F, the graphical user interface can include a graphical element 2144 allowing a user to select whether to modify factors for the given patient that can impact the probability 2130 or values for components 2132-2136. In response to a user selected the graphical element 2144, the computer system is instructed to access current data values for the given patient for medically modifiable factors such as the patient's weight, body mass index (BMI), physical activity level, diabetes control and smoking. Such values 2152, 2154, 2156, and 2158 can be presented in a display 2150 as indicated in FIG. 21D. The user can then make changes these values in the display 2150 as indicated in FIG. 21E. In the example in FIG. 21E, two of the values 2160 and 2162 have been changed. A user can the select a graphical element 2164 to request the computer system to compute and present updates values for the probability 2130 and for the components 2132-2136 based on these modifiable factors. The result of such an update is shown in FIG. 21F. In this example, a probability 2130 in FIG. 21B has been updated as indicated at 2172 and an amount of difference is shown at 2170. Similarly, the probabilities for improvement for components of this score can be updated.

It should be understood that the foregoing are merely illustrative examples of graphical user interfaces and that a wide variety of other user interfaces can be provided for presenting outputs of models, explainable factors of those models, and receiving data to be used in analyzing the explainable factors of those models.

The foregoing description is an example implementation of health care information system. The various computers used in this computer system can be implemented using one or more general purpose computers, such as client computers, server computers and database computers, which can be programmed to implement the functionality such as described in the example implementation. FIG. 6 is a block diagram of a general purpose computer with computer programs providing instructions to be executed by a processor in the general purpose computer. Computer programs on a general purpose computer generally include an operating system and applications. The operating system is a computer program running on the computer that manages access to various resources of the computer by the applications and the operating system. The various resources generally include memory, storage, communication interfaces, input devices and output devices.

Examples of such general purpose computers include, but are not limited to, larger computer systems such as server computers, database computers, desktop computers, laptop and notebook computers, as well as mobile or handheld computing devices, such as a tablet computer, hand held computer, smart phone, media player, personal data assistant, audio and/or video recorder, or wearable computing device.

Figure 6:
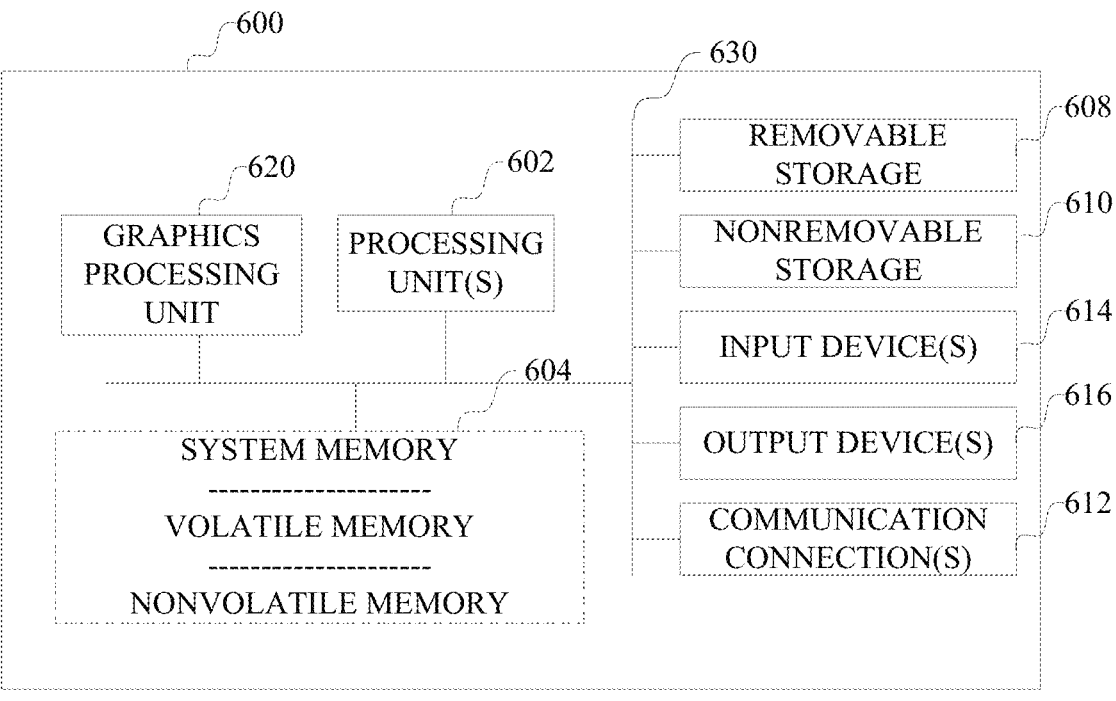
FIG. 6 is a block diagram of an example computer.

With reference to FIG. 6, an example computer 600 includes at least one processing unit 602 and memory 604. The computer can have multiple processing units 602 and multiple devices implementing the memory 604. A processing unit 602 can include one or more processing cores (not shown) that operate independently of each other. Additional co-processing units, such as graphics processing unit 620, also can be present in the computer. The memory 604 may include volatile devices (such as dynamic random access memory (DRAM) or other random access memory device), and non-volatile devices (such as a read-only memory, flash memory, and the like) or some combination of the two, and optionally including any memory available in a processing device. Other memory such as dedicated memory or registers also can reside in a processing unit. This configuration of memory is illustrated in FIG. 6 by dashed line 604. The computer 600 may include additional storage (removable and/or non-removable) including, but not limited to, magnetically-recorded or optically-recorded disks or tape. Such additional storage is illustrated in FIG. 6 by removable storage 608 and non-removable storage 610. The various components in FIG. 6 are generally interconnected by an interconnection mechanism, such as one or more buses 630.

A computer storage medium is any medium in which data can be stored in and retrieved from addressable physical storage locations by the computer. Computer storage media includes volatile and nonvolatile memory devices, and removable and non-removable storage devices. Memory 604 and 606, removable storage 608 and non-removable storage 610 are all examples of computer storage media. Some examples of computer storage media are RAM, ROM, EEPROM, flash memory or other memory technology, CD-ROM, digital versatile disks (DVD) or other optically or magneto-optically recorded storage device, magnetic cassettes, magnetic tape, magnetic disk storage or other magnetic storage devices. Computer storage media and communication media are mutually exclusive categories of media.

The computer 600 may also include communications connection(s) 612 that allow the computer to communicate with other devices over a communication medium. Communication media typically transmit computer program instructions, data structures, program modules or other data over a wired or wireless substance by propagating a modulated data signal such as a carrier wave or other transport mechanism over the substance. The term "modulated data signal" means a signal that has one or more of its characteristics set or changed in such a manner as to encode information in the signal, thereby changing the configuration or state of the receiving device of the signal. By way of example, and not limitation, communication media includes wired media such as a wired network or direct-wired connection, and wireless media include any non-wired communication media that allows propagation of signals, such as acoustic, electromagnetic, electrical, optical, infrared, radio frequency and other signals. Communications connections 612 are devices, such as a network interface or radio transmitter, that interface with the communication media to transmit data over and receive data from signals propagated through communication media.

The communications connections can include one or more radio transmitters for telephonic communications over cellular telephone networks, and/or a wireless communication interface for wireless connection to a computer network. For example, a cellular connection, a WiFi connection, a Bluetooth connection, and other connections may be present in the computer. Such connections support communication with other devices, such as to support voice or data communications.

The computer 600 may have various input device(s) 614 such as a various pointer (whether single pointer or multi-pointer) devices, such as a mouse, tablet and pen, touchpad and other touch-based input devices, stylus, image input devices, such as still and motion cameras, audio input devices, such as a microphone. The compute may have various output device(s) 616 such as a display, speakers, printers, and so on, also may be included. All of these devices are well known in the art and need not be discussed at length here.

The various storage 610, communication connections 612, output devices 616 and input devices 614 can be integrated within a housing of the computer, or can be connected through various input/output interface devices on the computer, in which case the reference numbers 610, 612, 614 and 616 can indicate either the interface for connection to a device or the device itself as the case may be.

An operating system of the computer typically includes computer programs, commonly called drivers, which manage access to the various storage 610, communication connections 612, output devices 616 and input devices 614. Such access generally includes managing inputs from and outputs to these devices. In the case of communication connections, the operating system also may include one or more computer programs for implementing communication protocols used to communicate information between computers and devices through the communication connections 612.

Any of the foregoing aspects may be embodied as a computer system, as any individual component of such a computer system, as a process performed by such a computer system or any individual component of such a computer system, or as an article of manufacture including computer storage in which computer program instructions are stored and which, when processed by one or more computers, configure the one or more computers to provide such a computer system or any individual component of such a computer system.

Each component (which also may be called a "module" or "engine" or the like), of a computer system such as described herein, and which operates on one or more computers, can be implemented using the one or more processing units of the computer and one or more computer programs processed by the one or more processing units. A computer program includes computer-executable instructions and/or computer-interpreted instructions, such as program modules, which instructions are processed by one or more processing units in the computer. Generally, such instructions define routines, programs, objects, components, data structures, and so on, that, when processed by a processing unit, instruct the processing unit to perform operations on data or configure the processor or computer to implement various components or data structures. A data structure is defined in a computer program and specifies how data is organized in storage, such as in a memory device or a storage device, so that the data can accessed, manipulated and stored.

It should be understood that the subject matter defined in the appended claims is not necessarily limited to the specific implementations described above. The specific implementations described above are disclosed as examples only.

What is claimed is:

1. A computer system, comprising:
   a. a processing system comprising a processing device and computer storage, wherein the computer storage stores:
      i. a first data structure including, for a plurality of entities, data values for input features for a trained computational model, wherein the data values for each entity are derived from a respective record for the entity in a data set, and
      ii. a second data structure including data identifying a selected subset of the input features for the trained computational model, the selected subset having fewer features than the input features;
   b. computer program code implementing the trained computational model which, when processed by the processing system, configures the processing system to apply input data values for the input features of a given entity to the trained computational model to output a predicted outcome for the given entity in response to the input data values for the input features of the entity;

c. computer program code that, when processed by the processing system, configures the processing system to generate a localized model for the given entity, wherein the localized model is distinct from and simplified with respect to the trained computational model and approximates the trained computational model, wherein the processing system generates the localized model based on a. the trained computational model and b. data values for the given entity from the first data structure for input features other than the selected subset of the input features identified by the second data structure, wherein the localized model has inputs and an output, wherein the inputs of the localized model correspond to only the selected subset of input features identified by the second data structure and the output of the localized model provides a predicted outcome for the given entity;

d. a sensitivity analysis module comprising computer program code that, when processed by the processing system, configures the processing system to analyze the localized model for the given entity by:

applying a plurality of different data values for the input features identified in the selected subset of the input features to the inputs of the localized model for the given entity, wherein the plurality of different data values are different from the data values for the selected subset of input features for the given entity as stored in the first data structure, whereby the localized model outputs respective predicted outcomes for the given entity for the different data values, and storing, in the computer storage, the respective predicted outcomes output from the localized model for the given entity; and e. a graphical user interface comprising computer program code that, when processed by the processing system, is responsive to the sensitivity analysis module to provide an output including human-understandable content describing how data values for the selected subset of input features likely would affect the predicted outcome of the trained computational model as applied to the given entity based on the stored respective predicted outcomes output from the localized model.

2. The computer system of claim 1, wherein the data set comprises health care information for a plurality of patients, wherein each patient in the plurality of patients has a respective record in the data set, and wherein the given entity is a given patient in the plurality of patients.

3. The computer system of claim 1, wherein the data set comprises health care information for a plurality of health care providers, wherein each health care provider in the plurality of health care providers has a respective record in the data set, and wherein the given entity is a given health care provider in the plurality of health care providers.

4. The computer system of claim 1, wherein the trained computational model is trained using a training set derived from the data set.

5. The computer system of claim 1, wherein the trained computational model performs classification of the entities into categories.

6. The computer system of claim 1, wherein the trained computational model computes risk factors associated with the entities.

7. The computer system of claim 1, wherein the entities are patients and the trained computational model computes predictions of outcomes for patients based on the records for the patients in the data set.

8. The computer system of claim 1, wherein the entities are patients and the trained computational model computes outcome scores for the patients based on the records for the patients in the data set.

9. The computer system of claim 8, wherein outcome scores are represented using an integer in a range of integer values.

10. The computer system of claim 1, wherein the entities are patients and the trained computational model computes factor scores for the patients based on the records for the patients in the data set.

11. The computer system of claim 1, wherein the second data structure comprises a library stored in the computer data storage including data representing the selected subset of input features.

12. The computer system of claim 11, wherein the selected subset of input features represented by the second data structure further correspond to actions which can be performed for the given entity.

13. The computer system of claim 12, wherein the library further includes a set of actionable factors, wherein the library stores, for each of the actionable factors, a mapping between the actionable factor and one or more respective input features in the selected subset of input features.

14. The computer system of claim 13, wherein the library further includes, for each actionable factor in the set of actionable factors, human-understandable content describing actions which can be performed for the given entity for output by the graphical user interface.

15. The computer system of claim 13, wherein the actionable factors include medically modifiable factors.

16. The computer system of claim 12, wherein the given entity comprises a patient and the actions include specifying a treatment for the patient.

17. The computer system of claim 12, wherein the given entity comprises a patient and the actions include specifying a behavior change for the patient.

18. The computer system of claim 1, wherein the sensitivity analysis module performs a sensitivity analysis on the localized model for the given entity wherein the first set of input features are held constant and sensitivity of the output of the localized model to variations in data values for the second set of input features is determined.

19. The computer system of claim 18 wherein the sensitivity analysis uses a linear regression model.

20. The computer system of claim 18 wherein the sensitivity analysis uses a nonlinear regression model.

21. The computer system of claim 18 wherein the sensitivity analysis uses a Bayesian model.

22. The computer system of claim 13, wherein the second data structure maps an input feature in the selected subset of input features to a respective data value for the input feature for use as the different data value for the input feature by the sensitivity analysis module.

23. The computer system of claim 1, wherein the second data structure maps an input feature in the selected subset of input features to a respective data value for the input feature for use as the different data value for the input feature by the sensitivity analysis module.

24. The computer system of claim 1, wherein the graphical user interface further configures the computer system to receive a data value for an input feature in the selected subset of input features for use as the different data value for that input feature by the sensitivity analysis module.

25. The computer system of claim 24, wherein, to receive the data value for the input feature, the graphical user interface configures the computer system to:
    access current data values for the given patient for medically modifiable factors;
    present the current data values in a display, and
    receive inputs indicating changes to the current data values.

26. The computer system of claim 25, wherein the medically modifiable factors include one or more of weight of a patient, body mass index of the patient, physical activity level of the patient, diabetes control of the patient, or smoking habits of the patient.

27. The computer system of claim 1 wherein the localized model is a linear model.

28. A computer system, comprising:
    a. a processing system comprising a processing device and computer storage, wherein the computer storage stores:
        i. a first data structure including, for each entity in a plurality of entities, respective data values for the entity for input features of a trained computational model, wherein the trained computational model outputs a predicted outcome for an entity based on the respective data values for the entity for the input features, and
        ii. a second data structure comprising data describing a set of actionable factors related to a selected subset of the input features, the selected subset having fewer features than the input features, the second data structure including, for each actionable factor:
            a) respective human-understandable content describing an action which can be performed for the given entity to affect the actionable factor, and
            b) a respective mapping between the actionable factor and one or more respective input features in the selected subset of input features; and
    b. computer program code that, when processed by the processing system, configures the processing system to:
    construct a localized model of the trained computational model for a given entity, wherein the localized model is equivalent to the trained computational model by having fixed values for input features based on the respective data values for the given entity from the first data structure for input features other than the selected subset of the input features identified by the second data structure, wherein the localized model has variable inputs corresponding to only the selected subset of input features identified by the second data structure and has an output providing a predicted outcome for the given entity,
    generate a respective predicted outcome for the given entity for different data values by applying the different data values for the input features identified in the selected subset of the input features to the variable inputs of the localized model for the given entity, wherein the different data values are different from the data values for the selected subset of input features for the given entity as stored in the first data structure; and
    c. a graphical user interface comprising computer program code that, when processed by the processing system, configures the processing system to:
    access current data values for the given entity for input features related to the actionable factors,
    apply the current data values to the input features of the trained computational model to cause the trained computational model to output a respective predicted outcome,
    present the current data values and the respective predictive outcome from the trained computational model in a display,
    receive an input indicating a change to at least one of the current data values to generate changed data values for at least one of the input features related to the actionable factors,
    cause the processing system to generate a predicted outcome output from the localized model for the given entity based on the changed data values by applying the changed data values as the different data values to the input features of the localized model for the given entity, and
    using the second data structure, output human-understandable content describing how the changed data values likely would affect the predicted outcome of the trained computational model as applied to the given entity based on the predicted outcome output from the localized model.

\* \* \* \* \*